US009803930B2

(12) United States Patent
Noureldin et al.

(10) Patent No.: US 9,803,930 B2
(45) Date of Patent: Oct. 31, 2017

(54) POWER GENERATION FROM WASTE HEAT IN INTEGRATED HYDROCRACKING AND DIESEL HYDROTREATING FACILITIES

(71) Applicant: Saudi Arabian Oil Company, Dhahran (SA)

(72) Inventors: Mahmoud Bahy Mahmoud Noureldin, Dhahran (SA); Hani Mohammed Al Saed, Jubail Ind. (SA); Ahmad Saleh Bunaiyan, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/087,329

(22) Filed: Mar. 31, 2016

(65) Prior Publication Data

US 2017/0058703 A1 Mar. 2, 2017

Related U.S. Application Data

(60) Provisional application No. 62/209,217, filed on Aug. 24, 2015, provisional application No. 62/209,147, (Continued)

(51) Int. Cl.
*F01K 13/02* (2006.01)
*F01K 3/18* (2006.01)
(Continued)

(52) U.S. Cl.
CPC ........... *F28D 7/0083* (2013.01); *B01D 3/007* (2013.01); *B01D 3/32* (2013.01); *B01D 51/10* (2013.01);
(Continued)

(58) Field of Classification Search
CPC ....... F01K 13/02; F01K 3/185; H02K 7/1823; C10G 65/00; F01D 17/145; F28D 7/0083
See application file for complete search history.

(56) References Cited

U.S. PATENT DOCUMENTS

| 3,995,428 A | 12/1976 | Roberts |
| 4,024,908 A | 5/1977 | Meckler |

(Continued)

FOREIGN PATENT DOCUMENTS

| CN | 1844325 | 10/2006 |
| CN | 101424453 | 5/2009 |

(Continued)

OTHER PUBLICATIONS

PCT International Search Report and Written Opinion of the International Searching Authority, PCT/US2016/048210, Dec. 22, 2016, 11 pages.

(Continued)

*Primary Examiner* — Viet Nguyen
(74) *Attorney, Agent, or Firm* — Fish & Richardson P.C.

(57) ABSTRACT

A power generation system includes a heating fluid circuit thermally coupled to multiple heat sources from at least an integrated hydrocracking plant and diesel hydro-treating plant of a petrochemical refining system. A first subset of the heat sources includes diesel hydro-treating plant heat exchangers coupled to streams in the diesel hydro-treating plant. A second subset of the heat sources includes hydrocracking plant heat exchangers coupled to streams in the hydrocracking plant. The heat exchangers are connected to a power generation system that includes an organic Rankine cycle (ORC) including a working fluid that is thermally coupled to the heating fluid circuit to heat the working fluid, an expander configured to generate electrical power from the heated first working fluid, and a control system configured to activate a set of control valves to selectively thermally couple the heating fluid circuit to at least a portion of the heat sources.

19 Claims, 10 Drawing Sheets

Related U.S. Application Data filed on Aug. 24, 2015, provisional application No. 62/209,188, filed on Aug. 24, 2015, provisional application No. 62/209,223, filed on Aug. 24, 2015.

(51) Int. Cl.

| | | |
|---|---|---|
| *H02K 7/18* | (2006.01) | |
| *C10G 65/00* | (2006.01) | |
| *F01D 17/14* | (2006.01) | |
| *F28D 7/00* | (2006.01) | |
| *C10G 45/02* | (2006.01) | |
| *C10G 35/04* | (2006.01) | |
| *C10L 3/10* | (2006.01) | |
| *C07C 7/08* | (2006.01) | |
| *C10G 65/12* | (2006.01) | |
| *C10G 33/06* | (2006.01) | |
| *B01D 3/00* | (2006.01) | |
| *B01D 3/32* | (2006.01) | |
| *B01D 51/10* | (2006.01) | |
| *B01D 53/047* | (2006.01) | |
| *B01D 53/14* | (2006.01) | |
| *B01D 53/18* | (2006.01) | |
| *B01D 53/34* | (2006.01) | |
| *B01D 53/48* | (2006.01) | |
| *B01D 53/86* | (2006.01) | |
| *B01D 53/96* | (2006.01) | |
| *C02F 1/58* | (2006.01) | |
| *C10G 45/44* | (2006.01) | |
| *C10G 47/00* | (2006.01) | |
| *F28F 9/26* | (2006.01) | |
| *C10G 69/00* | (2006.01) | |
| *F01K 25/06* | (2006.01) | |
| *F01K 25/08* | (2006.01) | |
| *F01K 27/02* | (2006.01) | |
| *F01K 13/00* | (2006.01) | |
| *F01K 23/06* | (2006.01) | |
| *C01B 3/24* | (2006.01) | |
| *C10G 45/00* | (2006.01) | |
| *C10K 3/04* | (2006.01) | |
| *F01K 27/00* | (2006.01) | |
| *C02F 101/10* | (2006.01) | |
| *C02F 101/16* | (2006.01) | |
| *C02F 103/18* | (2006.01) | |
| *C02F 103/36* | (2006.01) | |

(52) U.S. Cl.
CPC ....... *B01D 53/047* (2013.01); *B01D 53/1462* (2013.01); *B01D 53/185* (2013.01); *B01D 53/343* (2013.01); *B01D 53/48* (2013.01); *B01D 53/8603* (2013.01); *B01D 53/96* (2013.01); *C01B 3/24* (2013.01); *C02F 1/586* (2013.01); *C07C 7/08* (2013.01); *C10G 33/06* (2013.01); *C10G 35/04* (2013.01); *C10G 45/00* (2013.01); *C10G 45/02* (2013.01); *C10G 45/44* (2013.01); *C10G 47/00* (2013.01); *C10G 65/00* (2013.01); *C10G 65/12* (2013.01); *C10G 69/00* (2013.01); *C10K 3/04* (2013.01); *C10L 3/101* (2013.01); *C10L 3/103* (2013.01); *C10L 3/104* (2013.01); *F01D 17/145* (2013.01); *F01K 3/185* (2013.01); *F01K 13/00* (2013.01); *F01K 13/02* (2013.01); *F01K 23/06* (2013.01); *F01K 23/064* (2013.01); *F01K 25/06* (2013.01); *F01K 25/08* (2013.01); *F01K 27/00* (2013.01); *F01K 27/02* (2013.01); *F28F 9/26* (2013.01); *H02K 7/1823* (2013.01); *B01D 2252/204* (2013.01); *C01B 2203/0233* (2013.01); *C02F 2101/10* (2013.01); *C02F 2101/101* (2013.01); *C02F 2101/16* (2013.01); *C02F 2103/18* (2013.01); *C02F 2103/36* (2013.01); *C10G 2300/202* (2013.01); *C10G 2300/207* (2013.01); *C10G 2300/4006* (2013.01); *C10G 2300/4056* (2013.01); *C10G 2400/04* (2013.01); *C10G 2400/30* (2013.01); *C10L 2290/06* (2013.01); *C10L 2290/541* (2013.01); *Y02P 20/129* (2015.11)

(56) References Cited

U.S. PATENT DOCUMENTS

| | | | | |
|---|---|---|---|---|
| 4,109,469 | A | * | 8/1978 | Carson ............... F01K 7/18 60/651 |
| 4,291,232 | A | | 9/1981 | Cardone |
| 4,428,201 | A | | 1/1984 | Carson |
| 4,471,619 | A | | 9/1984 | Nolley, Jr. |
| 4,476,680 | A | | 10/1984 | Pollman |
| 4,512,155 | A | | 4/1985 | Sheinbaum |
| 4,792,390 | A | * | 12/1988 | Staggs ............... C10G 69/06 208/50 |
| 4,962,238 | A | | 10/1990 | Wolfe |
| 5,005,360 | A | | 4/1991 | McMurtry |
| 5,007,240 | A | | 4/1991 | Ishida |
| 5,164,070 | A | | 11/1992 | Munro |
| 5,240,476 | A | | 8/1993 | Hegarty |
| 5,497,624 | A | | 3/1996 | Amir |
| 5,562,190 | A | | 10/1996 | McArthur |
| 5,667,051 | A | | 9/1997 | Goldberg |
| 5,685,152 | A | | 11/1997 | Sterling |
| 5,740,677 | A | | 4/1998 | Vestesen |
| 5,804,060 | A | | 9/1998 | Benguigui et al. |
| 6,041,849 | A | | 3/2000 | Karl |
| 6,733,636 | B1 | | 5/2004 | Heins |
| 7,340,899 | B1 | | 3/2008 | Rubak |
| 8,046,999 | B2 | | 11/2011 | Doty |
| 8,529,202 | B2 | | 9/2013 | Zhang |
| 9,328,634 | B2 | | 5/2016 | Ikegami |
| 9,334,760 | B2 | | 5/2016 | Ernst |
| 9,518,497 | B2 | | 12/2016 | Tricaud |
| 9,562,201 | B2 | | 2/2017 | Noureldin |
| 2006/0010872 | A1 | | 1/2006 | Singh |
| 2008/0128134 | A1 | * | 6/2008 | Mudunuri ............ C10G 1/02 166/302 |
| 2008/0174115 | A1 | * | 7/2008 | Lambirth ............ E21B 36/04 290/2 |
| 2008/0289588 | A1 | | 11/2008 | Wees et al. |
| 2008/0307789 | A1 | | 12/2008 | Mak |
| 2008/0314726 | A1 | | 12/2008 | Choros |
| 2009/0000299 | A1 | | 1/2009 | Ast |
| 2009/0000906 | A1 | | 1/2009 | Petri |
| 2009/0071652 | A1 | * | 3/2009 | Vinegar ............ E21B 36/04 166/303 |
| 2009/0225929 | A1 | | 9/2009 | Genta et al. |
| 2009/0287029 | A1 | | 11/2009 | Anumakonda et al. |
| 2009/0301087 | A1 | * | 12/2009 | Borissov ............ E21B 41/00 60/641.2 |
| 2010/0076238 | A1 | | 3/2010 | Brandvold |
| 2010/0146974 | A1 | | 6/2010 | Ast |
| 2010/0242476 | A1 | | 9/2010 | Ast |
| 2010/0263380 | A1 | | 10/2010 | Biederman |
| 2010/0319346 | A1 | | 12/2010 | Ast |
| 2010/0326076 | A1 | | 12/2010 | Ast |
| 2010/0326098 | A1 | | 12/2010 | Rog |
| 2011/0016863 | A1 | | 1/2011 | Ernst |
| 2011/0041500 | A1 | | 2/2011 | Riley |
| 2011/0072819 | A1 | * | 3/2011 | Silva ............... F01K 23/065 60/651 |
| 2011/0072820 | A1 | | 3/2011 | Finkenrath |
| 2011/0083437 | A1 | | 4/2011 | Ast |
| 2011/0158858 | A1 | | 6/2011 | Alves |
| 2011/0203289 | A1 | | 8/2011 | Gutierrez |
| 2011/0314844 | A1 | | 12/2011 | Gu et al. |

(56) References Cited

U.S. PATENT DOCUMENTS

| | | | |
|---|---|---|---|
| 2012/0000175 | A1 | 1/2012 | Wormser |
| 2012/0031096 | A1* | 2/2012 | Ulas Acikgoz ......... F01K 25/08 60/651 |
| 2012/0047889 | A1 | 3/2012 | Ulas Acikgoz et al. |
| 2012/0085095 | A1 | 4/2012 | Penton et al. |
| 2012/0085096 | A1 | 4/2012 | Penton et al. |
| 2012/0085097 | A1 | 4/2012 | Penton et al. |
| 2012/0087783 | A1 | 4/2012 | Zhang |
| 2012/0131921 | A1 | 5/2012 | Held |
| 2012/0145050 | A1 | 6/2012 | Fisenko |
| 2012/0192563 | A1 | 8/2012 | Kauffman |
| 2012/0198768 | A1 | 8/2012 | Khosravian |
| 2012/0204817 | A1 | 8/2012 | Scherffius |
| 2012/0234263 | A1 | 9/2012 | Van Wees et al. |
| 2012/0279728 | A1* | 11/2012 | Northrop ........... B01D 53/1462 166/401 |
| 2012/0279900 | A1 | 11/2012 | Noureldin et al. |
| 2012/0285169 | A1 | 11/2012 | Freund |
| 2013/0047574 | A1 | 2/2013 | Kidambi |
| 2013/0062883 | A1 | 3/2013 | Kaneeda |
| 2013/0090395 | A1 | 4/2013 | DiGenova et al. |
| 2013/0091843 | A1 | 4/2013 | Zyhowski et al. |
| 2013/0104546 | A1 | 5/2013 | Goswami |
| 2013/0145763 | A1* | 6/2013 | Mirmobin ................. F22B 1/18 60/671 |
| 2013/0165534 | A1* | 6/2013 | McComish .............. C10G 2/32 518/702 |
| 2013/0213040 | A1 | 8/2013 | Goswami |
| 2013/0231909 | A1 | 9/2013 | Noureldin |
| 2013/0238154 | A1 | 9/2013 | Noureldin |
| 2013/0291808 | A1 | 11/2013 | Kautto |
| 2013/0334060 | A1* | 12/2013 | Koseoglu ................. C25B 1/10 205/637 |
| 2014/0090405 | A1 | 4/2014 | Held et al. |
| 2014/0174084 | A1 | 6/2014 | Kontomaris |
| 2014/0260311 | A1* | 9/2014 | Berlowitz ................. C01B 3/34 60/780 |
| 2014/0318124 | A1 | 10/2014 | Ernst |
| 2015/0027118 | A1 | 1/2015 | Tricaud |
| 2015/0073188 | A1 | 3/2015 | Floudas |
| 2015/0361831 | A1 | 12/2015 | Myers |
| 2015/0377079 | A1* | 12/2015 | Noureldin ................. C10J 3/82 60/671 |
| 2016/0032786 | A1 | 2/2016 | Zampieri |
| 2016/0045841 | A1* | 2/2016 | Kaplan ................ B01J 19/0093 429/49 |
| 2016/0076347 | A1 | 3/2016 | Diez |
| 2017/0058202 | A1 | 3/2017 | Noureldin |
| 2017/0058703 | A1 | 3/2017 | Noureldin |
| 2017/0058704 | A1 | 3/2017 | Noureldin |
| 2017/0058705 | A1 | 3/2017 | Noureldin |
| 2017/0058706 | A1 | 3/2017 | Noureldin |
| 2017/0058708 | A1 | 3/2017 | Noureldin |
| 2017/0058709 | A1 | 3/2017 | Noureldin |
| 2017/0058711 | A1 | 3/2017 | Noureldin |
| 2017/0058713 | A1 | 3/2017 | Noureldin |
| 2017/0058714 | A1 | 3/2017 | Noureldin |
| 2017/0058718 | A1 | 3/2017 | Noureldin |
| 2017/0058719 | A1 | 3/2017 | Noureldin |
| 2017/0058720 | A1 | 3/2017 | Noureldin |
| 2017/0058721 | A1 | 3/2017 | Noureldin |
| 2017/0058722 | A1 | 3/2017 | Noureldin |
| 2017/0058723 | A1 | 3/2017 | Noureldin |

FOREIGN PATENT DOCUMENTS

| | | |
|---|---|---|
| CN | 104560082 | 4/2015 |
| DE | 3731978 | 3/1988 |
| EP | 0292391 | 11/1988 |
| EP | 949318 | 10/1999 |
| EP | 2516326 | 10/2012 |
| FR | 2990990 A1 | 11/2013 |
| SU | 295317 | 10/1977 |
| WO | WO 97/21786 A1 | 6/1997 |
| WO | 2004102082 | 11/2004 |
| WO | 2011090553 | 7/2011 |
| WO | WO2012048132 A2 | 4/2012 |
| WO | WO2013055864 A1 | 4/2013 |
| WO | 2014205163 | 12/2014 |

OTHER PUBLICATIONS

PCT International Search Report and Written Opinion of the International Searching Authority, PCT/US2016/048224, Dec. 22, 2016, 11 pages.

PCT Intenational Search Report and Written Opinion of the International Searching Authority, PCT/US2016/048209, Dec. 22, 2016, 11 pages.

PCT International Search Report and Written Opinion of the International Searching Authority, PCT/US2016/048237, Dec. 22, 2016, 11 pages.

PCT International Search Report and Written Opinion of the International Searching Authority, PCT/US2016/048223, Dec. 22, 2016, 11 pages.

PCT International Search Report and Written Opinion of the International Searching Authority, PCT/US2016/048212, Dec. 22, 2016, 11 pages.

PCT International Search Report and Written Opinion of the International Searching Authority, PCT/US2016/027413, Nov. 22, 2016, 11 pages.

PCT International Search Report and Written Opinion of the International Searching Authority, PCT/US2016/048063, Nov. 23, 2016, 11 pages.

PCT International Search Report and Written Opinion of the International Searching Authority, PCT/US2016/048071, Nov. 23, 2016, 11 pages.

Hasan et al., "First and Second Law Analysis of a New Power and Refigeration Thermodynamic Cycle using a Solar Heat Source," Pergamon, Solar Energy, vol. 73, No. 5, Nov. 1, 2002, pp. 385-393.

Stecco, "Kalina Cycles: Some Possible Applications and Comments" Proceedings of the American Power Conference, XP 000609703, Jan. 1, 1993, vol. 1, pp. 196-201.

Tamm et al., "Theoretical and Experimental Investigation of an Ammonia-Water Power and Refrigeration Thermodynamic Cycle," Science Direct, Solar Energy, vol. 76, No. 1-3, Jan. 1, 2004, pp. 217-228.

Sadrameli et al., "Optimum Operating Conditions for a Combined Power and Cooling Thermodynamic Cycle," Science Direct, Applied Energy, vol. 84, No. 3, Nov. 10, 2006, pp. 254-265.

Vidal, "Analysis of a Combined Power and Refrigeration Cycle by the Exergy Method," Science Direct, Energy 31, Dec. 1, 2006, pp. 3401-3414.

PCT International Search Report and Written Opinion of the International Searching Authority, PCT/US2016/027417, Jul. 6, 2016, 11 pages.

PCT International Search Report and Written Opinion of the International Searching Authority, PCT/US2016/027797, Oct. 19, 2016, 12 pages.

PCT International Search Report and Written Opinion of the International Searching Authority, PCT/US2016/027794, Oct. 19, 2016, 13 pages.

PCT International Search Report and Written Opinion of the International Searching Authority, PCT/US2016/030063, Oct. 19, 2016, 13 pages.

PCT International Search Report and Written Opinion of the International Searching Authority, PCT/US2016/030156, Oct. 19, 2016, 12 pages.

PCT International Search Report and Written Opinion of the International Searching Authority, PCT/US2016/048074, Nov. 9, 2016, 12 pages.

PCT International Search Report and Written Opinion of the International Searching Authority, PCT/US2016/048042, Nov. 9, 2016, 12 pages.

PCT International Search Report and Written Opinion of the International Searching Authority, PCT/US2016/048219, Nov. 21, 2016, 13 pages.

(56) References Cited

OTHER PUBLICATIONS

PCT International Search Report and Written Opinion of the International Searching Authority, PCT/US2016/048229, Nov. 21, 2016, 13 pages.
PCT International Search Report and Written Opinion of the International Searching Authority, PCT/US2016/048236, Nov. 21, 2016, 13 pages.
PCT International Search Report and Written Opinion of the International Searching Authority, PCT/US2016/048067, Nov. 15, 2016, 11 pages.
PCT International Search Report and Written Opinion of the International Searching Authority, PCT/US2016/048066, Nov. 15, 2016, 11 pages.
PCT International Search Report and Written Opinion of the International Searching Authority, PCT/US2016/048078, Nov. 15, 2016, 12 pages.
PCT International Search Report and Written Opinion of the International Searching Authority, PCT/US2016/048076, Nov. 15, 2016, 12 pages.
PCT International Search Report and Written Opinion of the International Searching Authority, PCT/US2016/048207, Nov. 21, 2016, 12 pages.
"Organic Rankine Cycle," Choice of the Working Fluid, Wikipedia, published on or before Sep. 2014, 4 pages. http://en.wikipedia.org/wiki/Organic_Rankine_cycle?oldid=628773207.
Bourji et al., "Optimizing an Organic Rankine Cycle," CEP—Chemical Engineering Progress, Jan. 2013, 6 pages.
Handayani et al., "Opportunities for Organic Rankine Cycles (ORCs) in the Process Industries," Newcastle University, Oct. 25-26, 2011, 40 pages.
Kapil et al., "Advanced Process Integration for Low Grade Heat Recovery," published on or before Mar. 2010, 58 pages.
Meacher, Organic Rankine Cycle Systems for Waste Heat Recovery in Refineries and Chemical Process Plants, Proceedings from the Third Industrial Energy Technology Conference Houston, TX, Apr. 26-29, 1981, 8 pages.
Rowshanaie et al., "Generating the Electricity from Fluegas Produced by Boiler through a ORC Thermodynamic Cycle (Organic Rankine Cycle) by using a Shaft Tightness in Turbo-Expander," International Conference on Chemical, Agricultural and Medical Sciences, Dec. 29-30, 2013, 4 pages.
Tillman, "Low Temperature Waste Energy Recovery in Chemical Plants and Refineries," TAS Energy Inc., May 16, 2012, 11 pages.
Bertrand F. Tchanche, Gr. Lambrinos, A. Frangoudakis and G. Papadakis "Low-grade heat conversion into power using organic Rankine cycles—A review of various applications", Renewable and Sustainable Energy Reviews, 15 (2011) 3963-3979 (abstract provided, full article can be provided upon request).
Jung et al., "Feasibility assessment of refinery waste heat to power conversion using an organic Rankine cycle", Energy conversion and Management, vol. 77, published in 2014, pp. 396-407.
Jose Maria Ponce-Ortega, et al., "Optimal design of inter-plant waste energy integration", Applied Thermal Engineering, 62 (2014), 633-652 (abstract provided, full article can be provided upon request).
Levin J.DiGenova, Barbara B.Botros, and J.G. Brisson, "Method for customizing an organic Rankine cycle to a complex heat source for efficient energy conversion, demonstrated on a Fischer Tropsch plant", Applied energy, 102 (2013), 746-754 (abstract provided, full article can be provided upon request).

\* cited by examiner

US 9,803,930 B2

POWER GENERATION FROM WASTE HEAT IN INTEGRATED HYDROCRACKING AND DIESEL HYDROTREATING FACILITIES

CROSS-REFERENCE TO RELATED APPLICATIONS

This application claims priority under 35 U.S.C. §119 to U.S. Provisional Patent Application Ser. No. 62/209,217, filed on Aug. 24, 2015; U.S. Provisional Patent Application Ser. No. 62/209,147, filed on Aug. 24, 2015; U.S. Provisional Patent Application Ser. No. 62/209,188, filed on Aug. 24, 2015; and U.S. Provisional Patent Application Ser. No. 62/209,223, filed on Aug. 24, 2015. The entire contents of each of the preceding applications are incorporated herein by reference in their respective entireties.

TECHNICAL FIELD

This specification relates to power generation in industrial facilities.

BACKGROUND

Petroleum refining processes are chemical engineering processes and other facilities used in petroleum refineries to transform crude oil into products, for example, liquefied petroleum gas (LPG), gasoline, kerosene, jet fuel, diesel oils, fuel oils, and other products. Petroleum refineries are large industrial complexes that involve many different processing units and auxiliary facilities, for example, utility units, storage tanks, and other auxiliary facilities. Each refinery can have its own unique arrangement and combination of refining processes determined, for example, by the refinery location, desired products, economic considerations, or other factors. The petroleum refining processes that are implemented to transform the crude oil into the products such as those listed earlier can generate heat, which may not be re-used, and byproducts, for example, greenhouse gases (GHG), which may pollute the atmosphere. It is believed that the world's environment has been negatively affected by global warming caused, in part, due to the release of GHG into the atmosphere.

SUMMARY

This specification describes technologies relating to power generation from waste energy in industrial facilities. The present disclosure includes one or more of the following units of measure with their corresponding abbreviations, as shown in Table 1:

TABLE 1

| Unit of Measure | Abbreviation |
|---|---|
| Degrees Celsius | ° C. |
| Megawatts | MW |
| One million | MM |
| British thermal unit | Btu |
| Hour | h |
| Pounds per square inch (pressure) | psi |
| Kilogram (mass) | Kg |
| Second | S |

The details of one or more implementations of the subject matter described in this specification are set forth in the accompanying drawings and the description later. Other features, aspects, and advantages of the subject matter will become apparent from the description, the drawings, and the claims.

DETAILED DESCRIPTION

Figure 1A:
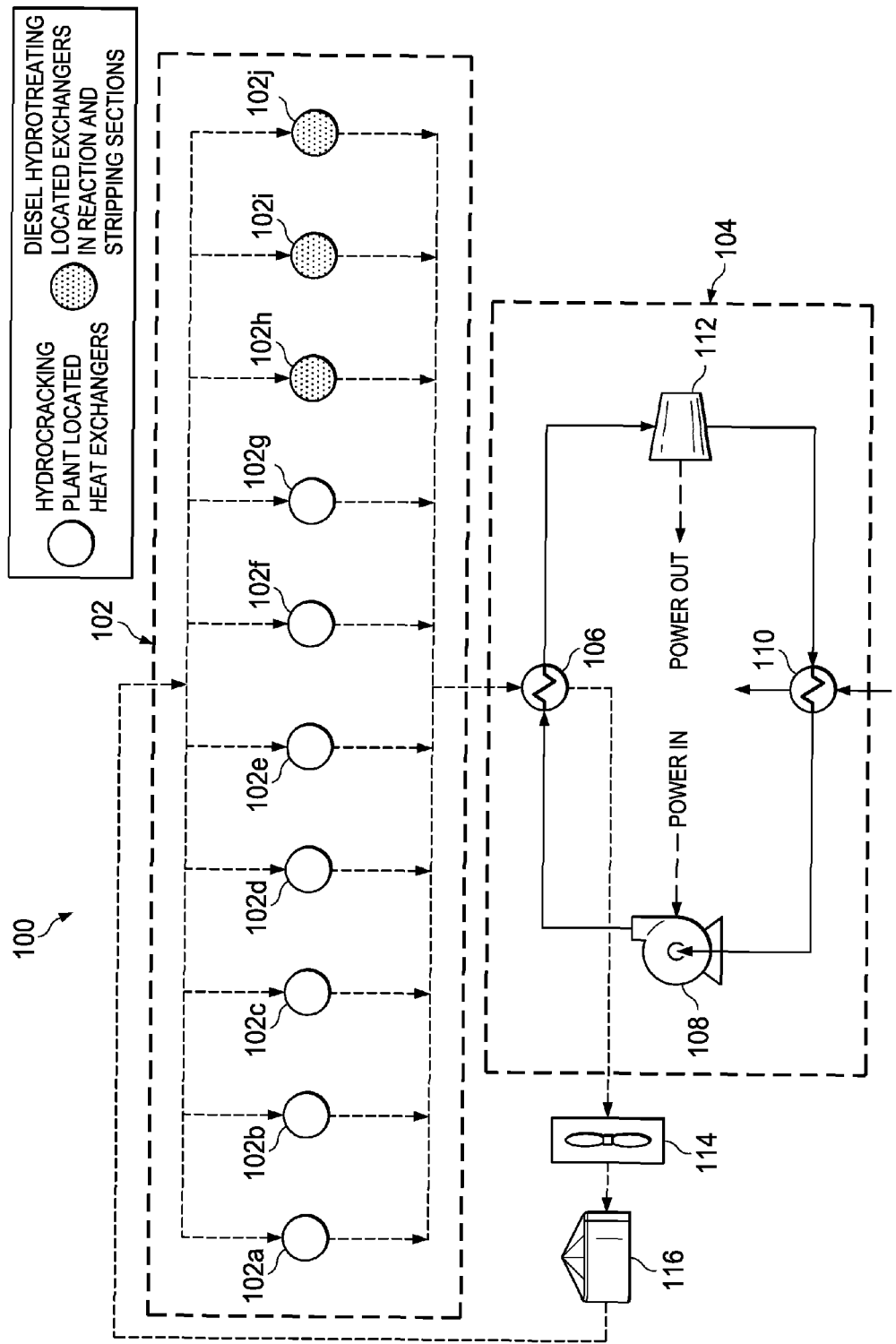
FIG. 1A is a schematic diagram of an example system to recover waste heat from ten heat sources.

Industrial waste heat is a source for potential carbon-free power generation in many industrial facilities, for example, crude oil refineries, petrochemical and chemical complexes, and other industrial facilities. For example, a medium-size integrated crude oil refinery with aromatics up to 4,000 MM Btu/h can be wasted to a network of air coolers extended along the crude oil and aromatics site. Some of the wasted heat can be used to power an Organic Rankine Cycle (ORC) machine, which uses an organic fluid such as refrigerants or hydrocarbons (or both) instead of water to generate power. ORC machines in combination with low temperature heat sources (for example, about or less than 232° C.) are being implemented as power generation systems. Optimizing ORC machines, for example, by optimizing the power generation cycle (that is, the Rankine cycle) or the organic fluid implemented by the ORC machine (or both), can improve power generation from recovered waste heat.

An industrial facility such as a petroleum refinery includes several sources of waste heat. One or more ORC machines can receive the waste heat from one or more or all of such sources. In some implementations, two or more sources of low grade heat can be consolidated by transferring heat from each of the sources to a common intermediate heat transfer medium (for example, water or other fluid). The intermediate heat transfer medium can then be used to evaporate the working fluid of the ORC machine to generate power, for example, to operate a turbine or other power generator. Such consolidation of sources of low grade heat can allow the ORC machine to be sized to realize greater efficiencies and economies of scale. Further, such a consolidated operation can improve flexibility in petroleum refinery design and plot space planning, since each heat source need not be in close proximity to the power generator. The proposed consolidation of heat sources, particularly, in mega sites such as a site-wide oil refinery that includes an aromatics complex and is the size of an eco-industrial park can represent an over-simplification of the problem of improving the process of recovering waste heat to generate power.

This disclosure describes optimizing power generation from waste heat, for example, low grade heat at a temperature at or less than 160° C., in large industrial facilities (for example, petroleum refineries or other large industrial refineries with several, sometimes more than 50, hot source streams) by utilizing a subset of all available hot source streams selected based, in part, on considerations for example, capital cost, ease of operation, economics of scale power generation, a number of ORC machines to be operated, operating conditions of each ORC machine, combinations of them, or other considerations. Recognizing that several subsets of hot sources can be identified from among the available hot sources in a large petroleum refinery, this disclosure describes selecting subsets of hot sources that are optimized to provide waste heat to one or more ORC machines for power generation. Further, recognizing that the utilization of waste heat from all available hot sources in a mega-site such as a petroleum refinery and aromatics complex is not necessarily or not always the best option, this disclosure identifies hot source units in petroleum refineries from which waste heat can be consolidated to power the one or more ORC machines.

This disclosure also describes modifying medium grade crude oil refining semi-conversion facilities and integrated medium grade crude oil refining semi-conversion and aromatics facilities plants' designs to improve their energy efficiencies relative to their current designs. To do so, new facilities can be designed or existing facilities can be re-designed (for example, retro-fitted with equipment) to recover waste heat, for example, low grade waste heat, from heat sources to power ORC machines. In particular, the existing design of a plant need not be significantly altered to accommodate the power generation techniques described here. The generated power can be used, in part, to power the facilities or transported to the electricity grid to be delivered elsewhere (or both).

By recovering all or part of the waste heat generated by one or more processes or facilities (or both) of industrial facilities and converting the recovered waste heat into power, carbon-free power (for example, in the form of electricity) can be generated for use by the community. The minimum approach temperature used in the waste heat recovery processes can be as low as 3° C. and the generated power can be as high as 80 MW. In some implementations, higher minimum approach temperatures can be used in an initial phase at the expense of less waste heat/energy recovery, while relatively better power generation (for example, in terms of economy of scale design and efficiency) is realized in a subsequent phase upon using the minimum approach temperature for the specific hot sources uses. In such situations, more power generation can be realized in the subsequent phase without needing to change the design topology of the initial phase or the subset of the low grade waste hot sources used in the initial phase (or both).

Not only pollution associated but also cost associated with power generation can be decreased. In addition, recovering waste heat from a customized group of hot sources to power one or more ORC machines is more optimal than recovering waste heat from all available hot sources. Selecting the hot sources in the customized group instead of or in addition to optimizing the ORC machine can improve or optimize (or both) the process of generating power from recovered waste heat. If a few number of hot sources are used for power generation, then the hot sources can be consolidated into few (for example, one or two) buffer streams using fluids, for example, hot oil or high pressure hot water system, or a mixture of the two.

In sum, this disclosure describes several petroleum refinery-wide separation/distillation networks, configurations, and processing schemes for efficient power generation using a basic ORC machine operating under specified conditions. The power generation is facilitated by obtaining all or part of waste heat, for example, low grade waste heat, carried by multiple, scattered low grade energy quality process streams. In some implementations, the ORC machine uses separate organic material to pre-heat the exchanger and evaporator and uses other organic fluid, for example, isobutane, at specific operating conditions.

Examples of Petroleum Refinery Plants

Industrial waste heat is a source for potential carbon-free power generation in many industrial facilities, for example, crude oil refineries, petrochemical and chemical complexes, and other industrial facilities. For example, a medium-size integrated crude oil refinery with aromatics up to 4,000 MM Btu/h can be wasted to a network of air coolers extended along the crude oil and aromatics site. Some of the wasted heat can be used to power an Organic Rankine Cycle (ORC) machine, which uses an organic fluid such as refrigerants or hydrocarbons (or both) instead of water to generate power. ORC machines in combination with low temperature heat sources (for example, about or less than 232° C.) are being implemented as power generation systems. Optimizing ORC machines, for example, by optimizing the power generation cycle (that is, the Rankine cycle) or the organic fluid implemented by the ORC machine (or both), can improve power generation from recovered waste heat.

An industrial facility such as a petroleum refinery includes several sources of waste heat. One or more ORC machines can receive the waste heat from one or more or all of such sources. In some implementations, two or more sources of low grade heat can be consolidated by transferring heat from each of the sources to a common intermediate heat transfer medium (for example, water or other fluid). The intermediate heat transfer medium can then be used to evaporate the working fluid of the ORC machine to generate power, for example, to operate a turbine or other power generator. Such consolidation of sources of low grade heat can allow the ORC machine to be sized to realize greater efficiencies and economies of scale. Further, such a consolidated operation can improve flexibility in petroleum refinery design and plot space planning, since each heat source need not be in close proximity to the power generator. The proposed consolidation of heat sources, particularly, in mega sites such as a site-wide oil refinery that includes an aromatics complex and is the size of an eco-industrial park can represent an over-simplification of the problem of improving the process of recovering waste heat to generate power.

This disclosure describes optimizing power generation from waste heat, for example, low grade heat at a temperature at or less than 160° C., in large industrial facilities (for example, petroleum refineries or other large industrial refineries with several, sometimes more than 50, hot source streams) by utilizing a subset of all available hot source streams selected based, in part, on considerations for example, capital cost, ease of operation, economics of scale power generation, a number of ORC machines to be operated, operating conditions of each ORC machine, combinations of them, or other considerations. Recognizing that several subsets of hot sources can be identified from among the available hot sources in a large petroleum refinery, this disclosure describes selecting subsets of hot sources that are optimized to provide waste heat to one or more ORC machines for power generation. Further, recognizing that the utilization of waste heat from all available hot sources in a mega-site such as a petroleum refinery and aromatics complex is not necessarily or not always the best option, this disclosure identifies hot source units in petroleum refineries from which waste heat can be consolidated to power the one or more ORC machines.

This disclosure also describes modifying medium grade crude oil refining semi-conversion facilities and integrated medium grade crude oil refining semi-conversion and aromatics facilities plants' designs to improve their energy efficiencies relative to their current designs. To do so, new facilities can be designed or existing facilities can be re-designed (for example, retro-fitted with equipment) to recover waste heat, for example, low grade waste heat, from heat sources to power ORC machines. In particular, the existing design of a plant need not be significantly altered to accommodate the power generation techniques described here. The generated power can be used, in part, to power the facilities or transported to the electricity grid to be delivered elsewhere (or both).

By recovering all or part of the waste heat generated by one or more processes or facilities of industrial facilities (or both) and converting the recovered waste heat into power, carbon-free power (for example, in the form of electricity) can be generated for use by the community. The minimum approach temperature used in the waste heat recovery processes can be as low as 3° C. and the generated power can be as high as 80 MW. In some implementations, higher minimum approach temperatures can be used in an initial phase at the expense of less waste heat/energy recovery, while relatively better power generation (for example, in terms of economy of scale design and efficiency) is realized in a subsequent phase upon using the minimum approach temperature for the specific hot sources uses. In such situations, more power generation can be realized in the subsequent phase without needing to change the design topology of the initial phase or the subset of the low grade waste hot sources used in the initial phase (or both).

Not only pollution associated but also cost associated with power generation can be decreased. In addition, recovering waste heat from a customized group of hot sources to power one or more ORC machines is more cost effective from a capital cost point-of-view than recovering waste heat from all available hot sources. Selecting the hot sources in the customized group instead of or in addition to optimizing the ORC machine can improve or optimize the process of generating power from recovered waste heat (or both). If a few number of hot sources are used for power generation, then the hot sources can be consolidated into few (for example, one or two) buffer streams using fluids, for example, hot oil or high pressure hot water system (or both).

In sum, this disclosure describes several petroleum refinery-wide separation/distillation networks, configurations, and processing schemes for efficient power generation using a basic ORC machine operating under specified conditions. The power generation is facilitated by obtaining all or part of waste heat, for example, low grade waste heat, carried by multiple, scattered low grade energy quality process streams. In some implementations, the ORC machine uses separate organic material to pre-heat the exchanger and evaporator and uses other organic fluid, for example, isobutane, at specific operating conditions.

Examples of Petroleum Refinery Plants

1. Hydrocracking Plant

Hydrocracking is a two-stage process combining catalytic cracking and hydrogenation. In this process heavy feedstocks are cracked in the presence of hydrogen to produce more desirable products. The process employs high pressure, high temperature, a catalyst, and hydrogen. Hydrocracking is used for feedstocks that are difficult to process by either catalytic cracking or reforming, since these feedstocks are characterized usually by high polycyclic aromatic content or high concentrations of the two principal catalyst poisons, sulfur and nitrogen compounds (or both).

The hydrocracking process depends on the nature of the feedstock and the relative rates of the two competing reactions, hydrogenation and cracking. Heavy aromatic feedstock is converted into lighter products under a wide range of high pressures and high temperatures in the presence of hydrogen and special catalysts. When the feedstock has a high paraffinic content, hydrogen prevents the formation of polycyclic aromatic compounds. Hydrogen also reduces tar formation and prevents buildup of coke on the catalyst. Hydrogenation additionally converts sulfur and nitrogen compounds present in the feedstock to hydrogen sulfide and ammonia. Hydrocracking produces isobutane for alkylation feedstock, and also performs isomerization for pour-point control and smoke-point control, both of which are important in high-quality jet fuel.

2. Diesel Hydrotreating Plant

Hydrotreating is a refinery process for reducing sulfur, nitrogen and aromatics while enhancing cetane number, density and smoke point. Hydrotreating assists the refining industry's efforts to meet the global trend for stringent clean fuels specifications, the growing demand for transportation fuels and the shift toward diesel. In this process, fresh feed is heated and mixed with hydrogen. Reactor effluent exchanges heat with the combined feed and heats recycle gas and stripper charge. Sulphide (for example, ammonium bisulphide and hydrogen sulphide) is then removed from the feed.

3. Aromatics Complex

A typical aromatics complex includes a combination of process units for the production of basic petrochemical intermediates of benzene, toluene and xylenes (BTX) using the catalytic reforming of naphtha using continuous catalyst regeneration (CCR) technology.

4. Naphtha Hydrotreating Plant and Continuous Catalytic Reformer Plants

A Naphtha Hydrotreater (NHT) produces 101 Research Octane Number (RON) reformate, with a maximum 4.0 psi Reid Vapor Pressure (RVP), as a blending stock in the gasoline pool. It usually has the flexibility to process blends of Naphtha from the Crude Unit, Gas Condensate Splitter, Hydrocracker, Light Straight-Run Naphtha (LSRN) and Visbreaker Plants. The NHT processes naphtha to produce desulfurized feed for the continuous catalyst regeneration (CCR) platformer and gasoline blending.

5. Crude Distillation Plant

Normally, a two-stage distillation plant processes various crude oils that are fractionated into different products, which are further processed in downstream facilities to produce liquefied petroleum gas (LPG), Naphtha, Motor Gasoline, Kerosene, Jet Fuel, Diesel, Fuel Oil and Asphalt. The Crude Distillation plant can typically process large volumes, for example, hundreds of thousands of barrels, of crude oil per day. During the summer months the optimum processing capacity may decrease. The plant can process mixture of crudes. The plant can also have asphalt producing facilities. The products from crude distillation plant are LPG, stabilized whole naphtha, kerosene, diesel, heavy diesel, and vacuum residuum. The Atmospheric Column receives the crude charge and separates it into overhead product, kerosene, diesel, and reduced crude. The Naphtha stabilizer may receive the atmospheric overhead stream and separates it into LPG and stabilized naphtha. The reduced crude is charged to the Vacuum tower where it is further separated into heavy diesel, vacuum gas oils and vacuum residuum.

6. Sour Water Stripping Utility Plant (SWSUP)

The SWSUP receives sour water streams from acid gas removal, sulfur recovery, and flare units, and the sour gas stripped and released from the soot water flash vessel. The SWSUP strips the sour components, primarily carbon dioxide ($CO_2$), hydrogen sulfide ($H_2S$) and ammonia ($NH_3$), from the sour water stream.

One of more of the refinery plants described earlier can supply heat, for example, in the form of low grade waste heat, to the ORC machine with reasonable economics of scale, for example, tens of megawatts of power. Studies have shown that particular refinery plants, for example, a hydrocracking plant, serve as good waste heat sources to generate power. However, in a study using only the hot source from the naphtha hydrotreating (NHT) plant, for example, at about 111° C., 1.7 MW of power was produced from about 27.6 MW of available waste heat at a low efficiency of about 6.2%. The low efficiency suggests that a hot source from the NHT plant alone is not recommended for waste heat generation due to high capital and economy of scale. In another study using one low grade hot source at about 97° C. from a crude distillation plant, 3.5 MW of power was produced from about 64.4 MW of available waste heat at a low efficiency of 5.3%. In a further study using one low grade hot source at about 120° C. from a sour water stripping plant, 2.2 MW of power was produced from about 32.7 MW of available waste heat at a low efficiency of 6.7%. These studies reveal that if waste heat recovery from a particular refinery plant to generate power is determined to be beneficial, it does not necessarily follow that waste heat recovery from any refinery plant will also be beneficial.

In another study, all waste heat available from all hot sources (totaling 11 hot source streams) in an aromatics complex were collected to generate about 13 MW of power from about 241 MW of available waste heat. This study reveals that using all available hot sources, while theoretically efficient, does not, in practice, necessarily translate to efficient power generation from available waste heat. Moreover, assembling power plants that can use all available hot sources can be very difficult considering the quantity of heat exchangers, pumps, and organic-based turbines (among other components and inter-connectors) involved. Not only will it be difficult to retrofit existing refineries to accommodate such power plants, but it will also be difficult to build such power plants from a grass roots stage. In the following sections, this disclosure describes combinations of hot sources selected from different refinery plants which can result in high efficiencies in generating power from available waste heat.

Even after identifying specific hot sources to be used for power generation in a mega-size site, there can be several combinations of hot sources that can be integrated for optimum generation of power using a specific ORC machine operating under specific conditions. Each of the following sections describes a specific combination of hot sources and a configuration for buffer systems which can be implemented with the specific combination to optimally generate power from waste heat with as minimum capital utilization as necessary. Also, the following sections describe two-buffer systems for low grade waste heat recovery where one-buffer systems for waste heat recovery as inapplicable. Each section describes the interconnections and related processing schemes between the different plants that make up the specific combination of hot sources, the configurations including components such as heat exchangers added in specific plants, at specific places and to specific streams in the process to optimize waste heat recovery and power generation. As described later, the different configurations can be implemented without changing the current layout or processes implemented by the different plants. The new configurations described in the sections later can generate between about 34 MW and about 80 MW of power from waste heat, enabling a proportional decrease of GHG emissions in petroleum refineries. The configurations described in the sections later demonstrate more than one way to achieve desired energy recovery using buffer systems. The configurations are related processing schemes do not impact and can be integrated with future potential in-plant energy saving initiatives, for example, low pressure steam generation. The configurations and processing schemes can render more than 10% first law efficiency for power generation from the low grade waste heat into the ORC machine.

Heat Exchangers

In the configurations described in this disclosure, heat exchangers are used to transfer heat from one medium (for example, a stream flowing through a plant in a crude oil refining facility, a buffer fluid or other medium) to another medium (for example, a buffer fluid or different stream flowing through a plant in the crude oil facility). Heat exchangers are devices which transfer (exchange) heat typically from a hotter fluid stream to a relatively less hotter fluid stream. Heat exchangers can be used in heating and cooling applications, for example, in refrigerators, air conditions or other cooling applications. Heat exchangers can be distinguished from one another based on the direction in which liquids flow. For example, heat exchangers can be parallel-flow, cross-flow or counter-current. In parallel-flow heat exchangers, both fluid involved move in the same direction, entering and exiting the heat exchanger side-by-side. In cross-flow heat exchangers, the fluid path runs perpendicular to one another. In counter-current heat exchangers, the fluid paths flow in opposite directions, with one fluid exiting whether the other fluid enters. Counter-current heat exchangers are sometimes more effective than the other types of heat exchangers.

In addition to classifying heat exchangers based on fluid direction, heat exchangers can also be classified based on their construction. Some heat exchangers are constructed of multiple tubes. Some heat exchangers include plates with room for fluid to flow in between. Some heat exchangers enable heat exchange from liquid to liquid, while some heat exchangers enable heat exchange using other media.

Heat exchangers in crude oil refining and petrochemical facilities are often shell and tube type heat exchangers which include multiple tubes through which liquid flows. The tubes are divided into two sets—the first set contains the liquid to be heated or cooled; the second set contains the liquid responsible for triggering the heat exchange, in other words, the fluid that either removes heat from the first set of tubes by absorbing and transmitting the heat away or warms the first set by transmitting its own heat to the liquid inside. When designing this type of exchanger, care must be taken in determining the correct tube wall thickness as well as tube diameter, to allow optimum heat exchange. In terms of flow, shell and tube heat exchangers can assume any of three flow path patterns.

Heat exchangers in crude oil refining and petrochemical facilities can also be plate and frame type heat exchangers. Plate heat exchangers include thin plates joined together with a small amount of space in between, often maintained by a rubber gasket. The surface area is large, and the corners of each rectangular plate feature an opening through which fluid can flow between plates, extracting heat from the plates as it flows. The fluid channels themselves alternate hot and cold liquids, meaning that the heat exchangers can effectively cool as well as heat fluid. Because plate heat exchangers have large surface area, they can sometimes be more effective than shell and tube heat exchangers.

Other types of heat exchangers can include regenerative heat exchangers and adiabatic wheel heat exchangers. In a regenerative heat exchanger, the same fluid is passed along both sides of the exchanger, which can be either a plate heat exchanger or a shell and tube heat exchanger. Because the fluid can get very hot, the exiting fluid is used to warm the incoming fluid, maintaining a near constant temperature. Energy is saved in a regenerative heat exchanger because the process is cyclical, with almost all relative heat being transferred from the exiting fluid to the incoming fluid. To maintain a constant temperature, a small quantity of extra energy is needed to raise and lower the overall fluid temperature. In the adiabatic wheel heat exchanger, an intermediate liquid is used to store heat, which is then transferred to the opposite side of the heat exchanger. An adiabatic wheel consists of a large wheel with treads that rotate through the liquids—both hot and cold—to extract or transfer heat. The heat exchangers described in this disclosure can include any one of the heat exchangers described earlier, other heat exchangers, or combinations of them.

Each heat exchanger in each configuration can be associated with a respective thermal duty (or heat duty). The thermal duty of a heat exchanger can be defined as an amount of heat that can be transferred by the heat exchanger from the hot stream to the cold stream. The amount of heat can be calculated from the conditions and thermal properties of both the hot and cold streams. From the hot stream point of view, the thermal duty of the heat exchanger is the product of the hot stream flow rate, the hot stream specific heat, and a difference in temperature between the hot stream inlet temperature to the heat exchanger and the hot stream outlet temperature from the heat exchanger. From the cold stream point of view, the thermal duty of the heat exchanger is the product of the cold stream flow rate, the cold stream specific heat and a difference in temperature between the cold stream outlet from the heat exchanger and the cold stream inlet temperature from the heat exchanger. In several applications, the two quantities can be considered equal assuming no heat loss to the environment for these units, particularly, where the units are well insulated. The thermal duty of a heat exchanger can be measured in watts (W), megawatts (MW), millions of British Thermal Units per hour (Btu/hr), or millions of kilocalories per hour (Kcal/h). In the configurations described here, the thermal duties of the heat exchangers are provided as being "about X MW," where "X" represents a numerical thermal duty value. The numerical thermal duty value is not absolute. That is, the actual thermal duty of a heat exchanger can be approximately equal to X, greater than X or less than X.

Flow Control System

In each of the configurations described later, process streams (also called "streams") are flowed within each plant in a crude oil refining facility and between plants in the crude oil refining facility. The process streams can be flowed using one or more flow control systems implemented throughout the crude oil refining facility. A flow control system can include one or more flow pumps to pump the process streams, one or more flow pipes through which the process streams are flowed and one or more valves to regulate the flow of streams through the pipes.

In some implementations, a flow control system can be operated manually. For example, an operator can set a flow rate for each pump and set valve open or close positions to regulate the flow of the process streams through the pipes in the flow control system. Once the operator has set the flow rates and the valve open or close positions for all flow control systems distributed across the crude oil refining facility, the flow control system can flow the streams within a plant or between plants under constant flow conditions, for example, constant volumetric rate or other flow conditions. To change the flow conditions, the operator can manually operate the flow control system, for example, by changing the pump flow rate or the valve open or close position.

In some implementations, a flow control system can be operated automatically. For example, the flow control system can be connected to a computer system to operate the flow control system. The computer system can include a computer-readable medium storing instructions (such as flow control instructions and other instructions) executable by one or more processors to perform operations (such as flow control operations). An operator can set the flow rates and the valve open or close positions for all flow control systems distributed across the crude oil refining facility using the computer system. In such implementations, the operator can manually change the flow conditions by providing inputs through the computer system. Also, in such implementations, the computer system can automatically (that is, without manual intervention) control one or more of the flow control systems, for example, using feedback systems implemented in one or more plants and connected to the computer system. For example, a sensor (such as a pressure sensor, temperature sensor or other sensor) can be connected to a pipe through which a process stream flows. The sensor can monitor and provide a flow condition (such as a pressure, temperature, or other flow condition) of the process stream to the computer system. In response to the flow condition exceeding a threshold (such as a threshold pressure value, a threshold temperature value, or other threshold value), the computer system can automatically perform operations. For example, if the pressure or temperature in the pipe exceeds the threshold pressure value or the threshold temperature value, respectively, the computer system can provide a signal to the pump to decrease a flow rate, a signal to open a valve to relieve the pressure, a signal to shut down process stream flow, or other signals.

This disclosure describes a waste heat recovery network that can be implemented to recover heat from a hydrocracking plant sub-unit and a hydro-treating plant sub-unit of a petrochemical refining system. As described later, heat recovered from the waste heat recovery network can be used to generate about 45 MW of power, thereby producing power from waste heat with a first law thermal efficiency of approximately 11.8%. The waste heat recovery network described here can be implemented either in its entirety or in phases. Each phase can be separately implemented without hindering previously implemented phases or future phases. The minimum approach temperature used in the waste heat recovery network described here can be as low as 3° C. Alternatively, higher minimum approach temperatures can be used in the beginning to achieve lower waste heat recovery. By decreasing the minimum approach temperature over time, reasonable power generation economies of scale can be used and higher power generation efficiency can be realized. Efficiency can also be increased by using a sub-set of the waste heat streams that are used in the network. The waste heat recovery network can be retrofitted to an existing petrochemical refining system layout, thereby decreasing a quantity of work needed to change the existing design topology of the petrochemical refining system.

The waste heat recovery network includes a heating fluid circuit thermally coupled to multiple heat sources, for example, ten heat sources, from a hydrocracking plant and a hydro-treating plant. The heat recovered using the waste heat recovery network can be provided to a power generation system that comprises an Organic Rankine Cycle (ORC). The design configuration of the waste heat recovery network and the processes implemented using the waste heat recovery network need not change with future efforts inside individual plants to enhance energy efficiency. The design configuration and the processes also need not be changed in response to other improvements to waste heat recovery in the petrochemical refining system. The waste heat recovery network uses low-low grade waste heat, that is, waste heat less than about 160° C.

Figure 1B:
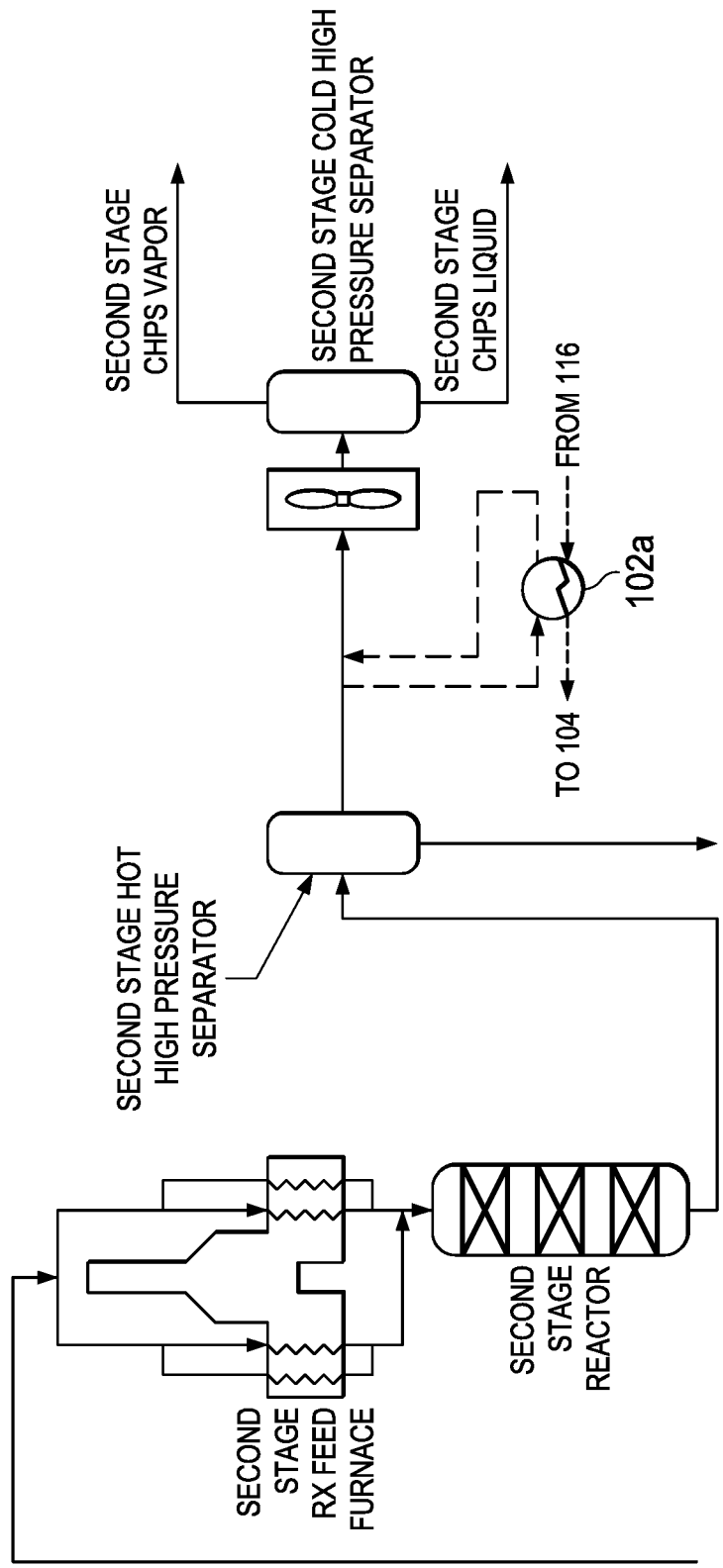
FIGS. 1B, 1C, 1DA and 1DB are schematic diagrams of seven heat sources in a hydrocracking plant.
Figure 1C:
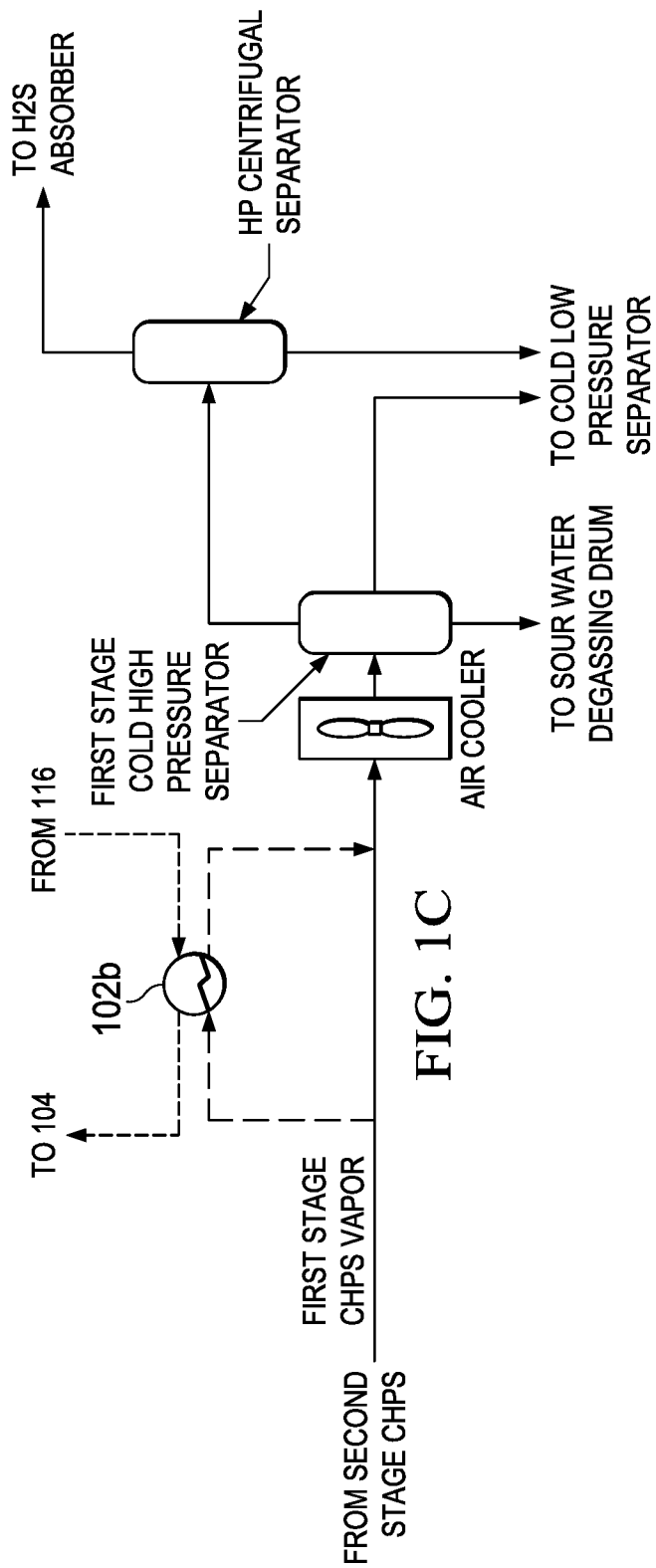
Figure 1D:
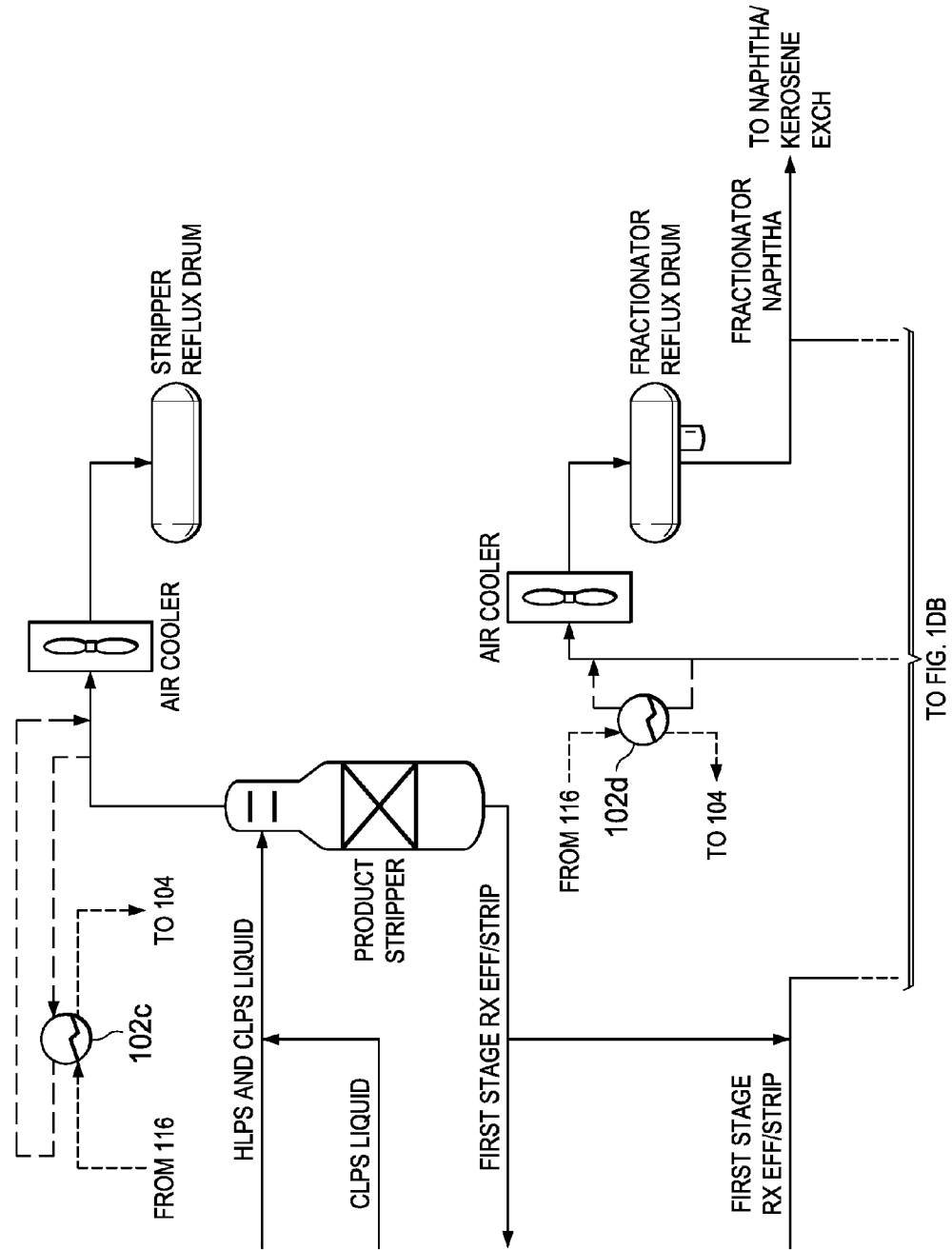
Figure 1D:
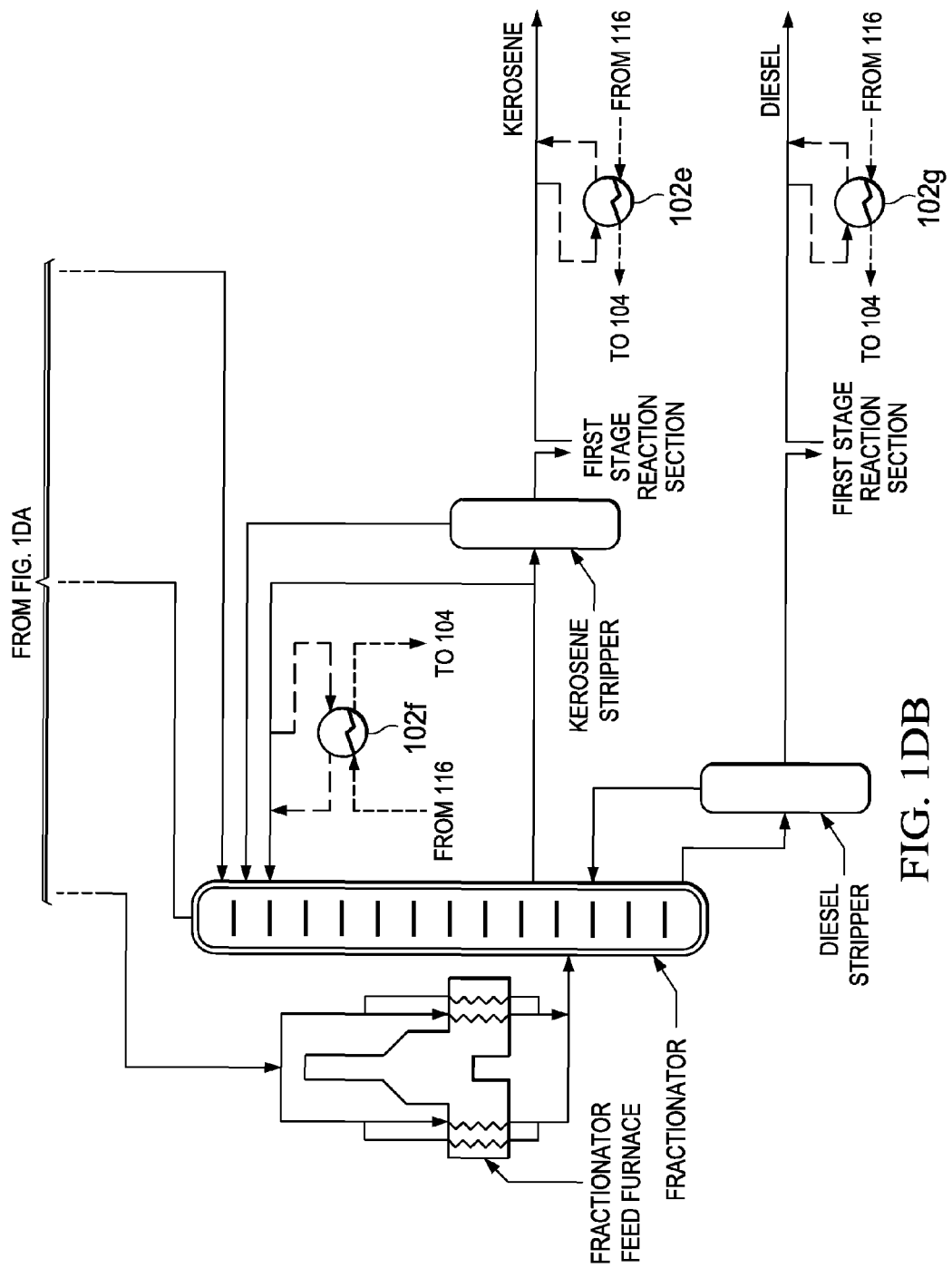
Figure 1E:
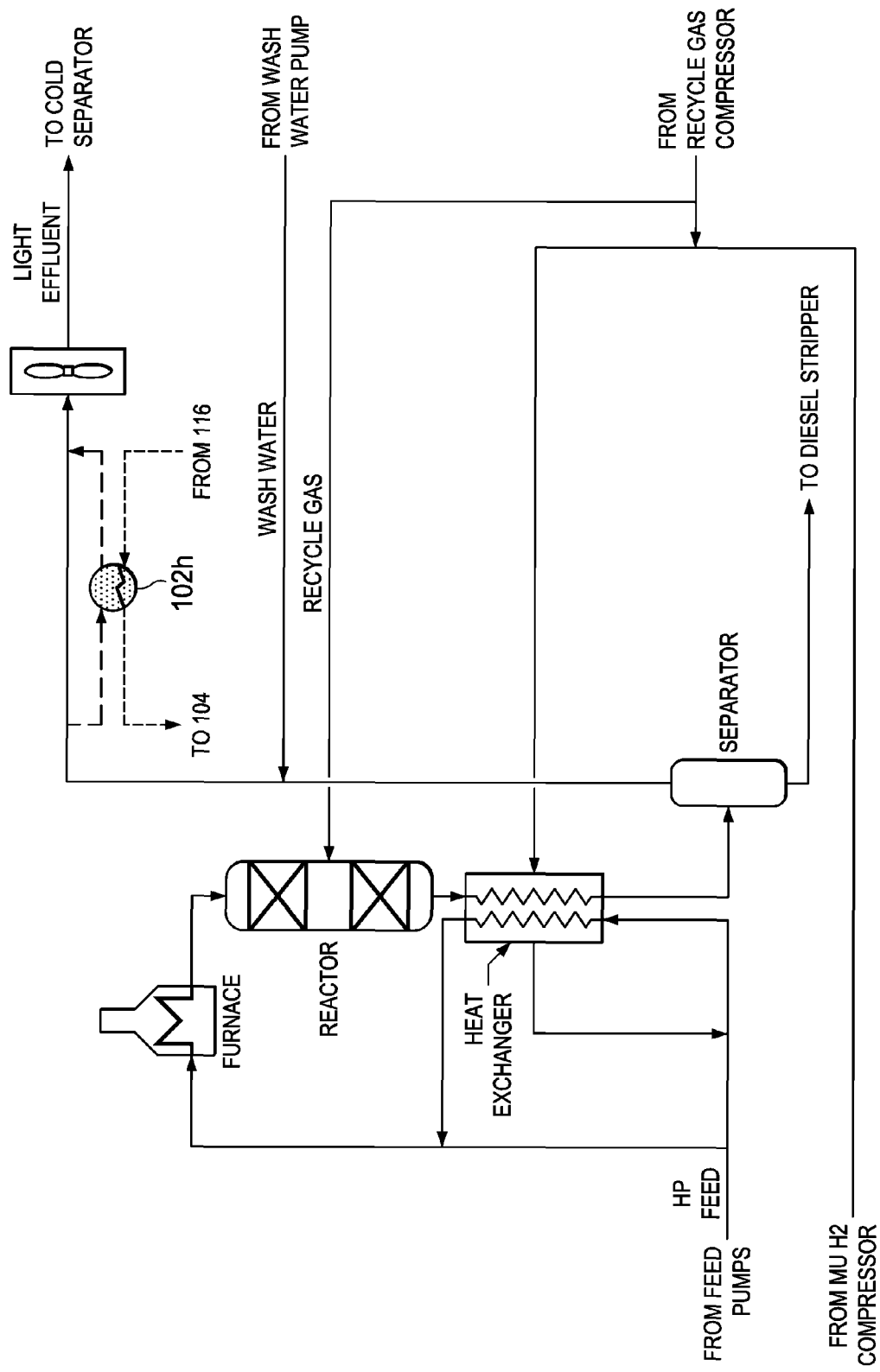
FIGS. 1E and 1F are schematic diagrams of three heat sources in a diesel hydro-treating plant.
Figure 1F:
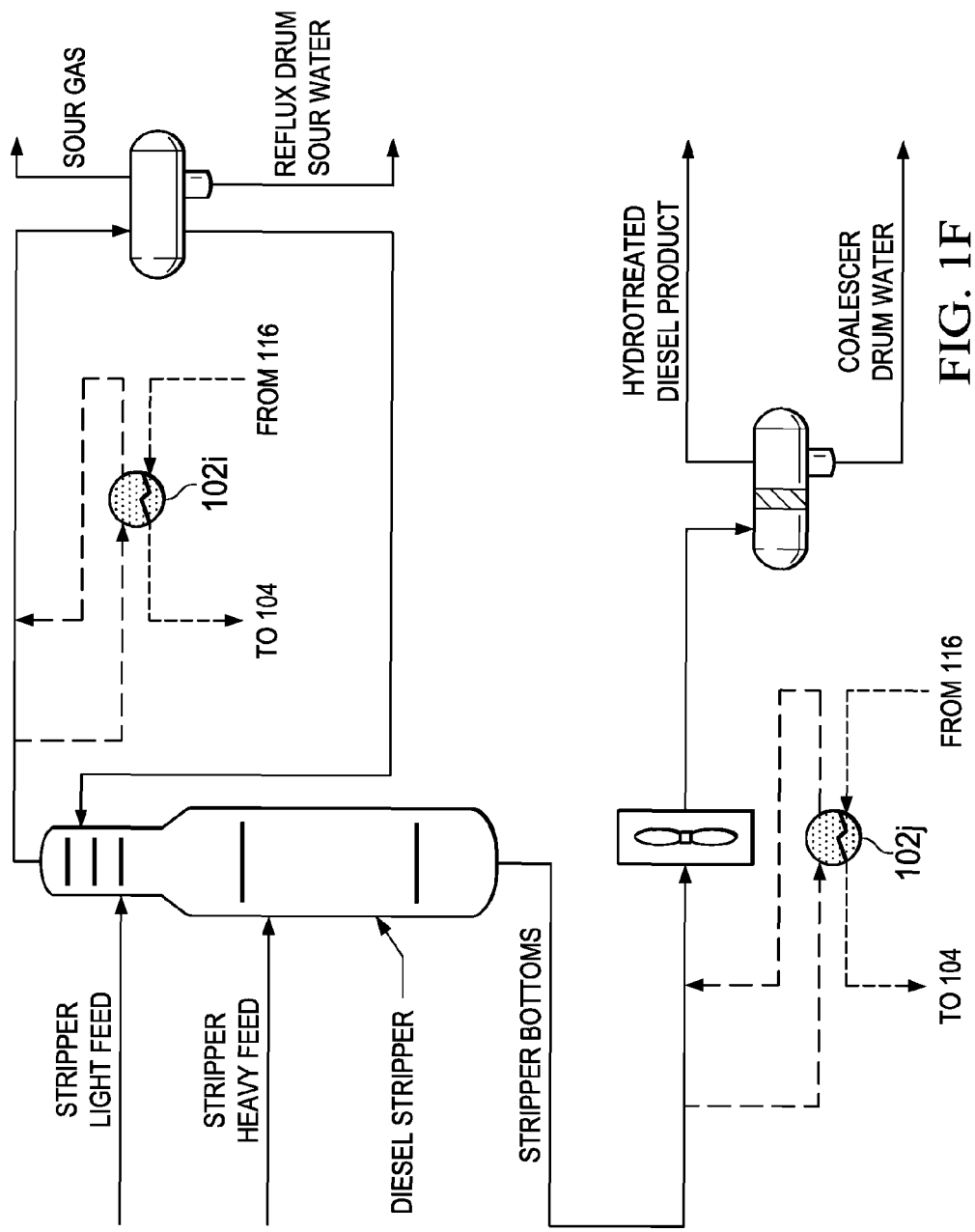
Figure 1G:
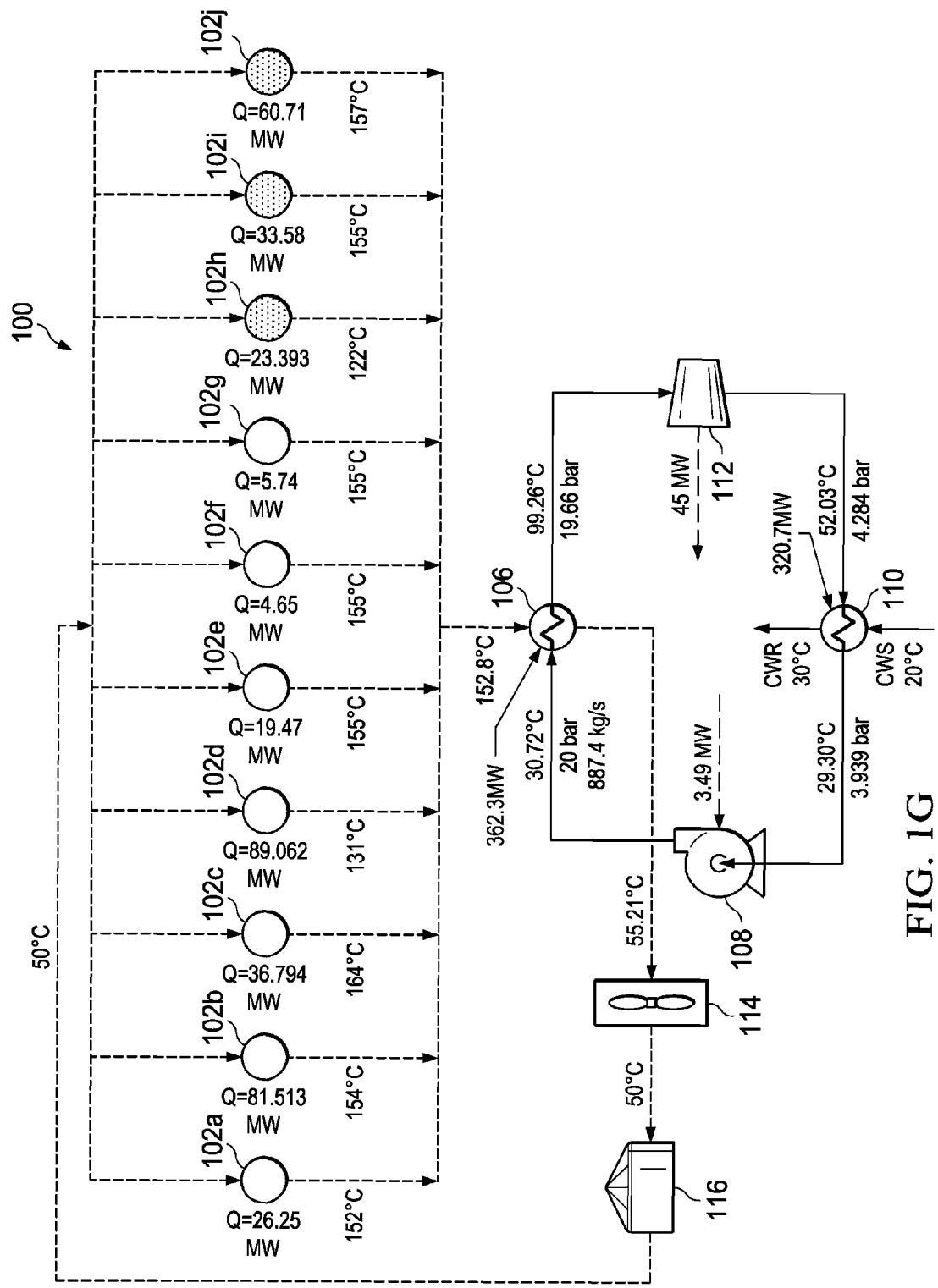
FIG. 1G is a schematic diagram of an implementation of the example network of FIG. 1A.

FIG. 1A is a schematic diagram of an example system 100 to recover waste heat from ten heat sources. FIGS. 1B-1D are schematic diagrams of seven heat sources in a hydrocracking plant. FIGS. 1E and 1F are schematic diagrams of three heat sources in a diesel hydro-treating plant. FIG. 1G is a schematic diagram of an implementation of the example network of FIG. 1A.

FIG. 1A is a schematic diagram of an example system 100 to recover waste heat from ten sources. In some implementations, the system 100 can include a heating fluid circuit 102 thermally coupled to multiple heat sources. For example, the multiple heat sources can include seven heat exchangers (a first heat exchanger 102a, a second heat exchanger 102b, a third heat exchanger 102c, a fourth heat exchanger 102d, a fifth heat exchanger 102e, a sixth heat exchanger 102f, and a seventh heat exchanger 102g) coupled to a hydrocracking plant of a petrochemical refining system. The multiple heat sources can also include three heat exchangers (an eighth heat exchanger 102h, a ninth heat exchanger 102i, and a tenth heat exchanger 102j) coupled to a diesel hydro-treating plant of the petrochemical refining system. In some implementations, the ten heat sources can be connected in parallel.

The example system 100 can include a power generation system 104 that includes an organic Rankine cycle (ORC). The ORC can include a working fluid that is thermally coupled to the heating fluid circuit 102 to heat the working fluid. In some implementations, the working fluid can be isobutane. The ORC can also include a gas expander 112 configured to generate electrical power from the heated working fluid. As shown in FIG. 1A, the ORC can additionally include an evaporator 106, a pump 108 and a condenser 110. In some implementations, the working fluid can be thermally coupled to the heating fluid circuit 102 in the evaporator 106.

In operation, a heating fluid (for example, water, oil, or other fluid) is circulated through the ten heat exchangers. An inlet temperature of the heating fluid that is circulated into the inlets of each of the ten heat sources is the same or substantially the same subject to any temperature variations that may result as the heating fluid flows through respective inlets. Each heat exchanger heats the heating fluid to a respective temperature that is greater than the inlet temperature. The heated heating fluids from the ten heat exchangers are combined and flowed through the evaporator 106 of the ORC. Heat from the heated heating fluid heats the working fluid of the ORC thereby increasing the working fluid temperature and evaporating the working fluid. The heat exchange with the working fluid results in a decrease in the temperature of the heating fluid. The heating fluid is then collected in a heating fluid tank 116 and can be pumped back through the ten heat exchangers to restart the waste heat recovery cycle. In some implementations, the heating fluid that exits the evaporator 106 can be flowed through an air cooler 114 to further cool the heating fluid before the heating fluid is collected in the heating fluid tank 116.

The heating fluid circuit to flow heating fluid through the ten heat exchangers can include multiple valves that can be operated manually or automatically. For example, the hydrocracking plant and the diesel hydro-treating plant can be fitted with the heating fluid flow pipes and valves. An operator can manually open each valve in the circuit to cause the heating fluid to flow through the circuit. To cease waste heat recovery, for example, to perform repair or maintenance or for other reasons, the operator can manually close each valve in the circuit. Alternatively, a control system, for example, a computer-controlled control system, can be connected to each valve in the circuit. The control system can automatically control the valves based, for example, on feedback from sensors (for example, temperature, pressure or other sensors), installed at different locations in the circuit. The control system can also be operated by an operator.

In the manner described earlier, the heating fluid can be looped through the ten heat exchangers to recover heat that would otherwise go to waste in the hydrocracking and diesel hydro-treating plants, and to use the recovered waste heat to operate the power generation system. By doing so, an amount of energy needed to operate the power generation system can be decreased while obtaining the same or substantially similar power output from the power generation system. For example, the power output from the power generation system that implements the waste heat recovery network can be higher or lower than the power output from the power generation system that does not implement the waste heat recovery network. Where the power output is less, the difference may not be statistically significant. Consequently, a power generation efficiency of the petrochemical refining system can be increased.

FIGS. 1B-1D are schematic diagrams of seven heat sources in a hydrocracking plant. FIG. 1B shows the first heat exchanger 102a in the hydrocracking plant of the petrochemical refining system. A feed stream from the $2^{nd}$ reaction section, $2^{nd}$ stage hot high pressure separator and the heating fluid flow through the first heat exchanger 102a simultaneously. The first heat exchanger 102a cools down the feed stream from a higher temperature, for example, about 157° C., to a lower temperature, for example, about 60° C., and increases the temperature of the heating fluid from a lower temperature, for example, from about 50° C., to a higher temperature, for example, about 152° C. The temperature of the heating fluid can be different from, for example, less than, 50° C. depending upon available cooling media temperatures in the condenser (for example, in cold weather countries) or more than 50° C. depending, for example, on design efficiencies or inefficiencies of the ORC system that render surplus heat available in the heating fluid stream after heating and vaporizing the working fluid in the ORC. In some implementations, a heating fluid temperature of about 50° C. can provide increased efficiency of waste heat to power conversion. The thermal duty of the first heat exchanger 102a to implement the heat exchange is about 26.25 MW. The heating fluid at 152° C. that exits the first heat exchanger 102a is circulated to a main header to be mixed with heated heating fluids from the other nine heat exchangers.

FIG. 1C shows the second heat exchanger 102b in the hydrocracking plant of the petrochemical refining system. A feed stream from the 1$^{st}$ reaction section, 1$^{st}$ stage cold high pressure separator and the heating fluid flow through the second heat exchanger 102b simultaneously. The second heat exchanger 102b cools down the feed stream from a higher temperature, for example, about 159° C., to a lower temperature, for example, about 60° C., and increases the temperature of the heating fluid from a lower temperature, for example, about 50° C., to a higher temperature, for example, about 154° C. The thermal duty of the second heat exchanger 102b to implement the heat exchange is about 81.51 MW. The heating fluid at 154° C. that exits the second heat exchanger 102b is circulated to the main header to be mixed with heated heating fluids from the other nine heat exchangers.

FIG. 1D shows the third heat exchanger 102c, the fourth heat exchanger 102d, the fifth heat exchanger 102e, the sixth heat exchanger 102f and the seventh heat exchanger 102g in the hydrocracking plant of the petrochemical refining system. A feed stream from the product stripper overhead and the heating fluid flow through the third heat exchanger 102c simultaneously. The third heat exchanger 102c cools down the feed stream from a higher temperature, for example, about 169° C., to a lower temperature, for example, about 60° C., and increases the temperature of the heating fluid from a lower temperature, for example, about 50° C., to a higher temperature, for example, about 164° C. The thermal duty of the third heat exchanger 102c to implement the heat exchange is about 36.8 MW. The heating fluid at 164° C. that exits the third heat exchanger 102c is circulated to the main header to be mixed with heated heating fluids from the other nine heat exchangers.

A feed stream from the main fractionator overhead and the heating fluid flow through the fourth heat exchanger 102d simultaneously. The fourth heat exchanger 102d cools down the feed stream from a higher temperature, for example, about 136° C., to a lower temperature, for example, about 60° C., and increases the temperature of the heating fluid from a lower temperature, for example, about 50° C., to a higher temperature, for example, about 131° C. The thermal duty of the fourth heat exchanger 102d to implement the heat exchange is about 89 MW. The heating fluid at 131° C. that exits the fourth heat exchanger 102d is circulated to the main header to be mixed with heated heating fluids from the other nine heat exchangers.

A kerosene product stream and the heating fluid flow through the fifth heat exchanger 102e simultaneously. The fifth heat exchanger 102e cools down the stream from a higher temperature, for example, about 160° C., to a lower temperature, for example, about 60° C., and increases the temperature of the heating fluid from a lower temperature, for example, about 50° C., to a higher temperature, for example, about 155° C. The thermal duty of the fifth heat exchanger 102e to implement the heat exchange is about 19.5 MW. The heating fluid at 155° C. that exits the fifth heat exchanger 102e is circulated to the main header to be mixed with heated heating fluids from the other nine heat exchangers.

A kerosene pumparound stream and the heating fluid flow through the sixth heat exchanger 102f simultaneously. The sixth heat exchanger 102f cools down the stream from a higher temperature, for example, about 160° C., to a lower temperature, for example, about 60° C., and increases the temperature of the heating fluid from a lower temperature, for example, about 50° C., to a higher temperature, for example, about 155° C. The thermal duty of the sixth heat exchanger 102f to implement the heat exchange is about 4.65 MW. The thermal duties of the heat exchangers can depend upon the heat capacity flow rates of the hot oil streams flowing through the heat exchangers. Therefore, in some instances, the thermal duties of two heat exchangers can be different even when the temperature changes of the heating fluid flowing through the two heat exchangers is the same. In such instances, the heat capacity flow rates of the two heat exchangers can be different. The heating fluid at 155° C. that exits the sixth heat exchanger 102f is circulated to the main header to be mixed with heated heating fluids from the other nine heat exchangers.

A diesel product stream and the heating fluid flow through the seventh heat exchanger 102g simultaneously. The seventh heat exchanger 102g cools down the stream from a higher temperature, for example, about 160° C., to a lower temperature, for example, about 60° C., and increases the temperature of the heating fluid from a lower temperature, for example, about 50° C., to a higher temperature, for example, about 155° C. The thermal duty of the seventh heat exchanger 102g to implement the heat exchange is about 5.74 MW. The heating fluid at 155° C. that exits the seventh heat exchanger 102g is circulated to the main header to be mixed with heated heating fluids from the other nine heat exchangers.

FIGS. 1E and 1F are schematic diagrams of three heat sources in a diesel hydro-treating plant. FIG. 1E shows the eighth heat exchanger 102h in the diesel hydro-treating plant of the petrochemical refining system. A stream from the light effluent to cold separator and the heating fluid flow through the eighth heat exchanger 102h simultaneously. The eighth heat exchanger 102h cools down the stream from a higher temperature, for example, about 127° C., to a lower temperature, for example, about 60° C., and increases the temperature of the heating fluid from a lower temperature, for example, from about 50° C., to a higher temperature, for example, about 122° C. The thermal duty of the eighth heat exchanger 102h to implement the heat exchange is about 23.4 MW. The heating fluid at 122° C. that exits the eighth heat exchanger 102h is circulated to the main header to be mixed with heated heating fluids from the other nine heat exchangers.

FIG. 1F shows the ninth heat exchanger 102i in the diesel hydro-treating plant of the petrochemical refining system. A stream from the diesel stripper overhead and the heating fluid flow through the ninth heat exchanger 102i simultaneously. The ninth heat exchanger 102i cools down the stream from a higher temperature, for example, about 160° C., to a lower temperature, for example, about 60° C., and increases the temperature of the heating fluid from a lower temperature, for example, from about 50° C., to a higher temperature, for example, about 155° C. The thermal duty of the ninth heat exchanger 102i to implement the heat exchange is about 33.6 MW. The heating fluid at 155° C. that exits the ninth heat exchanger 102i is circulated to the main header to be mixed with heated heating fluids from the other nine heat exchangers.

A diesel stripper product stream and the heating fluid flow through the tenth heat exchanger 102j simultaneously. The tenth heat exchanger 102j cools down the stream from a higher temperature, for example, about 162° C., to a lower temperature, for example, about 60° C., and increases the temperature of the heating fluid from a lower temperature, for example, from about 50° C., to a higher temperature, for example, about 157° C. The thermal duty of the tenth heat exchanger 102j to implement the heat exchange is about 60.7 MW. The heating fluid at 155° C. that exits the tenth heat exchanger 102h is circulated to the main header to be mixed with heated heating fluids from the other nine heat exchangers. The heat capacity flowrate values for the high pressure hot water system is split between the hydrocracking and the diesel hydro-treating plants. The flowrate values for the two plants are 2.56 MW/° C. and 1.14 MW/° C., respectively. The total hot oil heat capacity flow rate is 3.7 MW/° C. This steam heat capacity flow rate is divided into two streams. The first stream is directed to the hydrocracking plant with heat capacity flow rate equal to 2.56 MW/° C. and the second stream is directed to the diesel hydrotreating plant with a heat capacity flow rate equal to 1.14 MW/° C.

FIG. 1G is a schematic diagram of an implementation of the example system 100 of FIG. 1A. The heating fluids received from the ten heat exchangers are mixed in the main header resulting in a heating fluid at a temperature of about 153° C. The heating fluid is circulated through the evaporator 106 of the ORC. In some implementations, the evaporator 106 increases the temperature of the working fluid (for example, isobutane or other working fluid) from about 31° C. at 20 bar to about 99° C. at 20 bar at a thermal duty of about 362 MW. The gas expander 112 expands the high temperature, high pressure working fluid to generate power, for example, about 45 MW, at a turbine efficiency, for example, 85%. The expansion decreases the temperature and pressure of the working fluid, for example, to about 52° C. and about 4.3 bar, respectively. The working fluid flows through the condenser 110 which further decreases the temperature and pressure of the working fluid at a thermal duty of about 321 MW. For example, cooling fluid flows through the condenser 110 at a lower temperature, for example, 20° C., exchanges heat with the working fluid, and exits the condenser 110 at a higher temperature, for example, about 30° C. The cooled working fluid (for example, isobutane liquid) is pumped by the pump 108 at an efficiency, for example, of about 75%, and an input power, for example, of about 3.5 MW. The pump 108 increases the temperature of the working fluid to about 31° C. and pumps the working fluid at a mass flow rate of about 890 kg/s to the evaporator 106, which repeats the Rankine cycle to generate power.

Figure 1H:
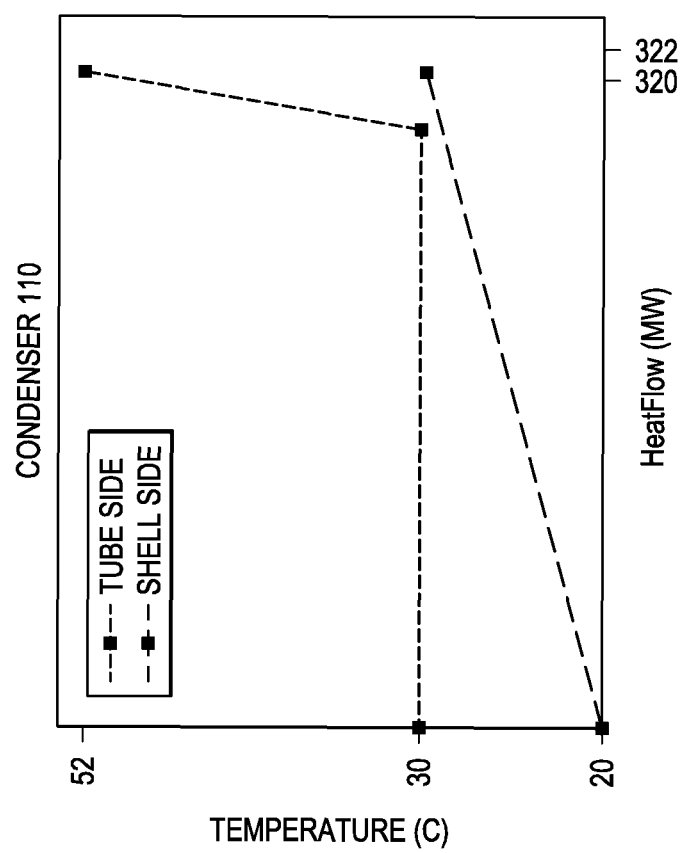
FIG. 1H is a graph that shows a tube-side fluid temperature and a shell-side fluid temperature in the condenser during an operation of the system described with reference to FIG. 1A.

FIG. 1H is a graph that shows a tube-side fluid temperature (for example, a cooling, or condenser, fluid flow) and a shell-side fluid temperature (for example, an ORC working fluid flow) in the condenser 110 during an operation of the system 100. This graph shows a temperature difference between the fluids on the y-axis relative to a heat flow between the fluids on the x-axis. For example, as shown in this figure, as the temperature difference between the fluids decreases, a heat flow between the fluids can increase. In some aspects, the cooling fluid medium may be at or about 20° C. or even higher. In such cases, a gas expander outlet pressure (for example, pressure of the ORC working fluid exiting the gas expander) may be high enough to allow the condensation of the ORC working fluid at the available cooling fluid temperature. As shown in FIG. 1H, the condenser water (entering the tubes of the condenser 110) enters at about 20° C. and leaves at about 30° C. The ORC working fluid (entering the shell-side of the condensers) enters as a vapor at about 52° C., and then condenses at 30° C. and leaves the condensers as a liquid at 30° C.

Figure 1I:
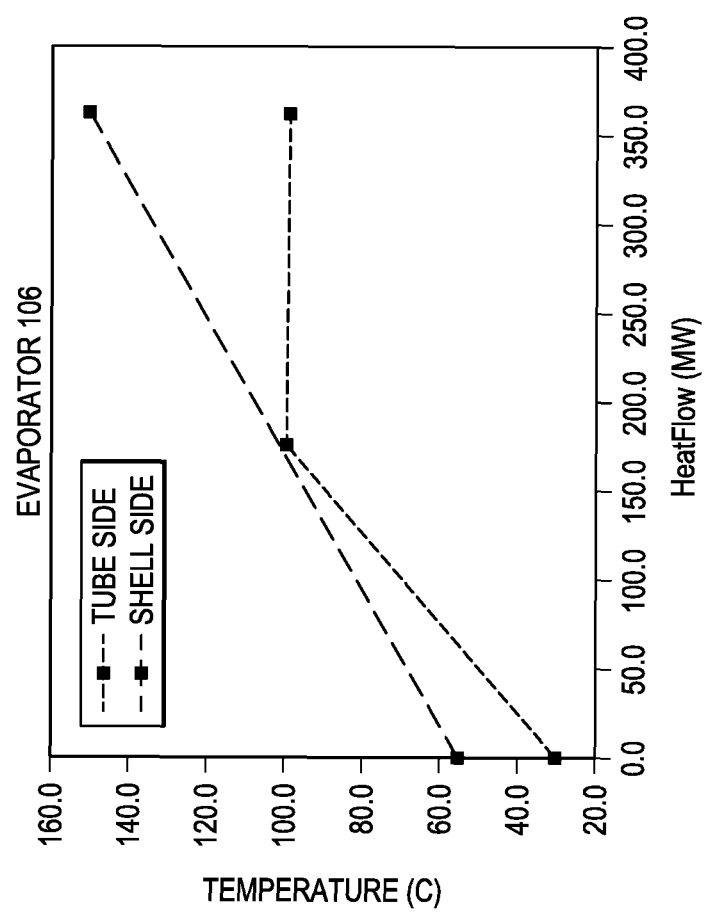
FIG. 1I is a graph that shows a tube-side fluid temperature and a shell-side fluid temperature in the evaporator during an operation of the system described with reference to FIG. 1A.

FIG. 1I is a graph that shows a tube-side fluid temperature (for example, a heating fluid flow) and a shell-side fluid temperature (for example, an ORC working fluid flow) in the evaporator 106 during an operation of the system 100. This graph shows a temperature difference between the fluids on the y-axis relative to a heat flow between the fluids on the x-axis. For example, as shown in this figure, as the temperature difference between the fluids decreases, a heat flow between the fluids can increase. This graph shows a temperature difference between the fluids on the y-axis relative to a heat flow between the fluids on the x-axis. For example, as shown in FIG. 1I, as the tube-side fluid (for example, the hot oil or water in the heating fluid circuit 102) is circulated through the evaporator 106, heat is transferred from that fluid to the shell-side fluid (for example, the ORC working fluid). Thus, the tube-side fluid enters the evaporator 106 at about 152° C. and leaves the evaporator 106 at about 55° C. The shell-side fluid enters the evaporator 106 at about 30° C. (for example, as a liquid) and leaves the evaporator 106 at about 99° C. (for example, as a vapor with some superheating).

The techniques to recover heat energy generated by a petrochemical refining system described earlier can be implemented in at least one or both of two example scenarios. In the first scenario, the techniques can be implemented in a petrochemical refining system that is to be constructed. For example, a geographic layout to arrange multiple sub-units of a petrochemical refining system can be identified. The geographic layout can include multiple sub-unit locations at which respective sub-units are to be positioned. Identifying the geographic layout can include actively determining or calculating the location of each sub-unit in the petrochemical refining system based on particular technical data, for example, a flow of petrochemicals through the sub-units starting from crude petroleum and resulting in refined petroleum. Identifying the geographic layout can alternatively or in addition include selecting a layout from among multiple previously-generated geographic layouts. A first subset of sub-units of the petrochemical refining system can be identified. The first subset can include at least two (or more than two) heat-generating sub-units from which heat energy is recoverable to generate electrical power. In the geographic layout, a second subset of the multiple sub-unit locations can be identified. The second subset includes at least two sub-unit locations at which the respective sub-units in the first subset are to be positioned. A power generation system to recover heat energy from the sub-units in the first subset is identified. The power generation system can be substantially similar to the power generation system described earlier. In the geographic layout, a power generation system location can be identified to position the power generation system. At the identified power generation system location, a heat energy recovery efficiency is greater than a heat energy recovery efficiency at other locations in the geographic layout. The petrochemical refining system planners and constructors can perform modeling or computer-based simulation experiments (or both) to identify an optimal location for the power generation system to maximize heat energy recovery efficiency, for example, by minimizing heat loss when transmitting recovered heat energy from the at least two heat-generating sub-units to the power generation system. The petrochemical refining system can be constructed according to the geographic layout by positioning the multiple sub-units at the multiple sub-unit locations, positioning the power generation system at the power generation system location, interconnecting the multiple sub-units with each other such that the interconnected multiple sub-units are configured to refine petrochemicals, and interconnecting the power generation system with the sub-units in the first subset such that the power generation system is configured to recover heat energy from the sub-units in the first subset and to provide the recovered heat energy to the power generation system. The power generation system is configured to generate power using the recovered heat energy.

In the second scenario, the techniques can be implemented in an operational petrochemical refining system. In other words, the power generation system described earlier can be retrofitted to an already constructed and operational petrochemical refining system.

Implementations of the subject matter described here can increase an energy output of petrochemical refining systems by about 41.6 MW for local utilization or export to an electricity grid. In this manner, the carbon consumption and GHG emissions of the plant can be decreased.

Thus, particular implementations of the subject matter have been described. Other implementations are within the scope of the following claims.

What is claimed is:

1. A power generation system comprising:
a heating fluid circuit thermally coupled to a plurality of heat sources from a plurality of sub-units of a petrochemical refining system, wherein the plurality of sub-units comprises a hydrocracking plant and a diesel hydro-treating plant,
wherein a first subset of the plurality of heat sources comprises a plurality of diesel hydro-treating plant heat exchangers coupled to streams in the diesel hydro-treating plant,
wherein a second subset of the plurality of heat sources comprises a plurality of hydrocracking plant heat exchangers coupled to streams in the hydrocracking plant, wherein each hydrocracking plant heat exchanger comprises a respective stream circulated through the hydrocracking plant and a portion of the heating fluid,
wherein:
a first hydrocracking plant heat exchanger exchanges heat between a 2nd reaction section, 2nd stage cold high pressure separator feed stream and a portion of the heating fluid,
a second hydrocracking plant heat exchanger exchanges heat between a 1st reaction section, 1st stage cold high pressure separator feed stream and a portion of the heating fluid,
a third hydrocracking plant heat exchanger exchanges heat between a product stripper overhead stream and a portion of the heating fluid,
a fourth hydrocracking plant heat exchanger exchanges heat between a main fractionator overhead stream and a portion of the heating fluid,
a fifth hydrocracking plant heat exchanger exchanges heat between a kerosene product stream and a portion of the heating fluid,
a sixth hydrocracking plant heat exchanger exchanges heat between a kerosene pump around stream and a portion of the heating fluid, and
a seventh hydrocracking plant heat exchanger exchanges heat between a diesel product stream and a portion of the heating fluid;
a first power generation system that comprises an organic Rankine cycle (ORC), the ORC comprising (i) a working fluid that is thermally coupled to the heating fluid circuit to heat the working fluid, and (ii) an expander configured to generate electrical power from the heated working fluid; and
a control system configured to activate a set of control valves to selectively thermally couple the heating fluid circuit to at least a portion of the plurality of heat sources.

2. The system of claim 1, wherein the working fluid is thermally coupled to the heating fluid circuit in an evaporator of the ORC.

3. The system of claim 2, wherein the working fluid comprises isobutane.

4. The system of claim 1, wherein the heating fluid circuit comprises a heating fluid tank that is fluidly coupled to the heating fluid circuit.

5. The system of claim 1, wherein the plurality of heat sources comprises ten heat sources, wherein the first subset comprises three diesel hydro-treating plant heat exchangers and the second subset comprises seven hydrocracking plant heat exchangers.

6. The system of claim 1, wherein each diesel hydro-treating plant heat exchanger comprises a respective stream circulated through the diesel hydro-treating plant and a portion of the heating fluid.

7. The system of claim 6, wherein:
a first diesel hydro-treating plant heat exchanger exchanges heat between a light effluent to cold separator stream and a portion of the heating fluid,
a second diesel hydro-treating plant heat exchanger exchanges heat between a diesel stripper overhead stream and a portion of the heating fluid, and
a third diesel hydro-treating plant heat exchanger exchanges heat between a diesel stripper product stream and a portion of the heating fluid.

8. The system of claim 1, wherein the plurality of heat sources are fluidly coupled in parallel.

9. The system of claim 1, wherein the heating fluid circuit comprises water or oil.

10. The system of claim 1, wherein the first power generation system is on-site at the petrochemical refining system.

11. The system of claim 1, wherein the first power generation system is configured to generate about 45 MW of power.

12. A method of recovering heat energy generated by a petrochemical refining system, the method comprising:
identifying a geographic layout to arrange a plurality of sub-units of a petrochemical refining system, the geographic layout including a plurality of sub-unit locations at which the respective plurality of sub-units are to be positioned, wherein the plurality of sub-units comprises a hydrocracking plant and a diesel hydro-treating plant;
identifying a first subset of the plurality of sub-units of the petrochemical refining system, the first subset including a plurality of diesel hydro-treating plant heat exchangers coupled to streams in the diesel hydro-treating plant and a plurality of hydrocracking plant heat exchangers coupled to streams in the hydrocracking plant, wherein heat energy is recoverable from the first subset of the plurality of sub-units to generate electrical power;
identifying, in the geographic layout, a second subset of the plurality of sub-unit locations, the second subset including sub-unit locations at which the respective sub-units in the first subset are to be positioned;
identifying a power generation system to recover heat energy from the sub-units in the first subset, the power generation system comprising:
a heating fluid circuit fluidly connected to the sub-units in the first subset;
a first power generation system that comprises an organic Rankine cycle (ORC), the ORC comprising (i) a working fluid that is thermally coupled to the heating fluid circuit to heat the working fluid, and (ii) an expander configured to generate electrical power from the heated working fluid; and a control system configured to activate a set of control valves to selectively thermally couple the heating fluid circuit to the first subset;

identifying, in the geographic layout, a power generation system location to position the power generation system, wherein a heat energy recovery efficiency at the power generation system location is greater than a heat energy recovery efficiency at other sub-unit locations within the geographic layout, operating the petrochemical refining system to refine petrochemicals;

operating the power generation system to:
recover heat energy from the sub-units in the first subset through the heating fluid circuit;
provide the recovered heat energy to the power generation system; and
generate power using the recovered heat energy; and wherein each hydrocracking plant heat exchanger comprises a respective stream circulated through the hydrocracking plant and a portion of the heating fluid, and wherein operating the petrochemical refining system to refine petrochemicals comprises:

operating a first hydrocracking plant heat exchanger to exchange heat between a 2nd reaction section, 2nd stage cold high pressure separator feed stream and a portion of the heating fluid, operating a second hydrocracking plant heat exchanger to exchange heat between a 1st reaction section, 1st stage cold high pressure separator feed stream and a portion of the heating fluid, operating a third hydrocracking plant heat exchanger to exchange heat between a product stripper overhead stream and a portion of the heating fluid, operating a fourth hydrocracking plant heat exchanger to exchange heat between a main fractionator overhead stream and a portion of the heating fluid, operating a fifth hydrocracking plant heat exchanger to exchange heat between a kerosene product stream and a portion of the heating fluid, operating a sixth hydrocracking plant heat exchanger to exchange heat between a kerosene pump around stream and a portion of the heating fluid, and operating a seventh hydrocracking plant heat exchanger to exchange heat between a diesel product stream and a portion of the heating fluid.

13. The method of claim 12, further comprising constructing the petrochemical refining system according to the geographic layout by positioning the plurality of sub-units at the plurality of sub-unit locations, positioning the power generation system at the power generation system location, interconnecting the plurality of sub-units with each other such that the interconnected plurality of sub-units are configured to refine petrochemicals, and interconnecting the power generation system with the sub-units in the first subset such that the power generation system is configured to recover heat energy from the sub-units in the first subset and to provide the recovered heat energy to the power generation system, the power generation system configured to generate power using the recovered heat energy.

14. The method of claim 12, further comprising thermally coupling the working fluid to the heating fluid circuit in an evaporator of the ORC.

15. The method of claim 12, wherein each diesel hydro-treating plant heat exchanger comprises a respective stream circulated through the diesel hydro-treating plant and a portion of the heating fluid, and wherein operating the petrochemical refining system to refine petrochemicals comprises:

operating a first diesel hydro-treating plant heat exchanger to exchange heat between a light effluent to cold separator stream and a portion of the heating fluid, operating a second diesel hydro-treating plant heat exchanger to exchange heat between a diesel stripper overhead stream and a portion of the heating fluid, and operating a third diesel hydro-treating plant heat exchanger to exchange heat between a diesel stripper product stream and a portion of the heating fluid.

16. The method of claim 12, further comprising operating the power generation system to generate about 45 MW of power.

17. A method of re-using heat energy generated by an operational petrochemical refining system, the method comprising:

identifying a geographic layout that comprises an arrangement of a plurality of sub-units of an operational petrochemical refining system, the geographic layout including a plurality of sub-units, each positioned at a respective sub-unit location, wherein the plurality of sub-units comprises a hydrocracking plant and a diesel hydro-treating plant;

identifying a first subset of the plurality of sub-units of the petrochemical refining system, the first subset including a plurality of diesel hydro-treating plant heat exchangers coupled to streams in the diesel hydro-treating plant and a plurality of hydrocracking plant heat exchangers coupled to streams in the hydrocracking plant, wherein heat energy is recoverable from the first subset of the plurality of sub-units to generate electrical power;

identifying, in the geographic layout, a second subset of the plurality of sub-unit locations, the second subset sub-unit locations at which the respective sub-units in the first subset have been positioned;

identifying a power generation system to recover heat energy from the sub-units in the first subset, the power generation system comprising:
a heating fluid circuit fluidly connected to the sub-units in the first subset;
a first power generation system that comprises an organic Rankine cycle (ORC), the ORC comprising (i) a working fluid that is thermally coupled to the heating fluid circuit to heat the working fluid, and (ii) an expander configured to generate electrical power from the heated working fluid; and
a control system configured to activate a set of control valves to selectively thermally couple the heating fluid circuit to at least a portion of the plurality of heat sources;

identifying a power generation system location in the operational petrochemical refining system to position the power generation system, wherein a heat energy recovery efficiency at the power generation system location is greater than a heat energy recovery efficiency at other sub-unit locations within the operational petrochemical refining system; and operating the power generation system to:
recover heat energy from the sub-units in the first subset through the heating fluid circuit;
provide the recovered heat energy to the power generation system; and
generate power using the recovered heat energy, wherein each hydrocracking plant heat exchanger comprises a respective stream circulated through the hydrocracking plant and a portion of the heating fluid, and wherein the method further comprises:

operating a first hydrocracking plant heat exchanger to exchange heat between a $2^{nd}$ reaction section, $2^{nd}$ stage cold high pressure separator feed stream and a portion of the heating fluid, operating a second hydrocracking plant heat exchanger to exchange heat between a $1^{st}$ reaction section, $1^{st}$ stage cold high pressure separator feed stream and a portion of the heating fluid, operating a third hydrocracking plant heat exchanger to exchange heat between a product stripper overhead stream and a portion of the heating fluid, operating a fourth hydrocracking plant heat exchanger to exchange heat between a main fractionator overhead stream and a portion of the heating fluid, operating a fifth hydrocracking plant heat exchanger to exchange heat between a kerosene product stream and a portion of the heating fluid, operating a sixth hydrocracking plant heat exchanger to exchange heat between a kerosene pump around stream and a portion of the heating fluid, and operating a seventh hydrocracking plant heat exchanger to exchange heat between a diesel product stream and a portion of the heating fluid.

18. The method of claim 17, further comprising interconnecting the power generation system with the sub-units in the first subset such that the power generation system is configured to recover heat energy from the sub-units in the first subset and to provide the recovered heat energy to the power generation system, the power generation system is configured to generate power using the recovered heat energy.

19. The method of claim 17, wherein each diesel hydro-treating plant heat exchanger comprises a respective stream circulated through the diesel hydro-treating plant and a portion of the heating fluid, and wherein the method further comprises:

operating a first diesel hydro-treating plant heat exchanger to exchange heat between a light effluent to cold separator stream and a portion of the heating fluid, operating a second diesel hydro-treating plant heat exchanger to exchange heat between a diesel stripper overhead stream and a portion of the heating fluid, and operating a third diesel hydro-treating plant heat exchanger to exchange heat between a diesel stripper product stream and a portion of the heating fluid.

* * * * *